US006057424A

United States Patent [19]
Vail, III

[11] Patent Number: 6,057,424
[45] Date of Patent: May 2, 2000

[54] METHOD AND APPARATUS TO SYNTHESIZE DNA AND DNA-LIKE MOLECULAR STRUCTURES BY APPLYING ELECTRIC FIELDS TO GASEOUS MIXTURES OF CHEMICAL REACTANTS CONTAINING TEMPLATE PARTICULATE MATTER

[76] Inventor: William Banning Vail, III, 3123 198th Pl SE., Bothell, Wash. 98012

[21] Appl. No.: 08/840,124

[22] Filed: Mar. 24, 1997

[51] Int. Cl.$^7$ .............................. A61K 38/00; C07H 21/00
[52] U.S. Cl. .............................. 530/333; 435/6; 435/91.1; 435/91.5; 536/25.3
[58] Field of Search .............................. 435/6, 91.1, 91.5, 435/810; 436/501; 536/22.1, 23.1, 24.1, 24.3–24.33, 25.3; 530/300, 350, 333, 338; 935/88

[56] References Cited

U.S. PATENT DOCUMENTS

| | | | |
|---|---|---|---|
| 3,629,083 | 12/1971 | Brendle | 204/165 |
| 4,574,038 | 3/1986 | Wan | 204/162 R |
| 5,002,652 | 3/1991 | Nelson et al. | 204/412 |

OTHER PUBLICATIONS

Acton, et al., *Cold Cathode Discharge Tubes*, Academic Press Inc., New York, NY, pp. 1–9, pp. 122–151, and pp. 200–227, 1963.

Aldridge, *The Thread of Life, The Story of Genes and Genetic Engineering*, Cambridge University Press, Cambridge, Great Britain, pp. 1–258, 1996.

Allegre, et al., "The Evolution of the Earth", Scientific American, vol. 271, No. 4, pp. 66–75, Oct. 1994.

American Petroleum Institute, *Reference Clay Minerals, American Petroleum Institute Research Project 49*, Columbia University Press, New York, NY, 1951; Report No. 1, pp. 1–66; Report No. 2, pp. 39–76; Report No. 3, pp. 25–37 and pp. 45–48; Report No. 4, p. 69 and p. 101; Report No. 5, p. 1, pp. 7–10, pp. 33–41, and pp. 50–58; Report No. 6, pp. 1–4, pp. 11–12, and pp. 16–17; Report No. 7, pp. 1–160; and Report No. 8, pp. 3–13, p. 24, pp. 28–30, and pp. 68–72.

Audesirk, et al., *Biology, Life on Earth*, Prentice Hall, Upper Saddle River, New Jersey, 4th Edition, pp. 535–555, 1996.

Bernal, *The Origin of Life*, The World Publishing Company, Cleveland, Ohio, pp. 1–345, 1967.

Bernal, "The Physical Basis of Life", The Proceedings of The Physical Society, vol. 62, Part 9, No. 357A, pp. 537–558, 1949.

Cairns–Smith, *Genetic Takeover and the Mineral Origins of Life*, Cambridge University Press, Cambridge, Great Britain, pp. 1–477, 1982.

Cairns–Smith, *Seven Clues to the Origin of Life*, Cambridge University Press, Cambridge, Great Britain, pp. 1–131, 1985.

Campbell, et al., "Sheep Cloned by Nuclear Transfer from a Cultured Cell Line", Nature, vol. 380, pp. 64–66, 1996.

Chang, "The Planetary Setting of Prebiotic Evolution", *Early Life on Earth*, Nobel Symposium No. 84, Columbia University Press, New York, NY, pp. 10–23, 1994.

Cowen, *History of Life*, Blackwell Scientific Publications, Boston, MA, 2nd Edition, pp. 1–26, 1995.

Dandliker, et al., "Oxidative Thymine Dimer Repair in the DNA Helix", Science, vol. 275, pp. 1465–1468, Mar. 7, 1997.

(List continued on next page.)

*Primary Examiner*—Ardin H. Marschel

[57] ABSTRACT

The methods to synthesize these chemicals in a laboratory are theorized to be related to natural processes that resulted in the creation of primordial life in the early atmosphere of Earth. The theory of the origin of primordial life in the Earth's early atmosphere is derived from an earlier U.S. Disclosure Document entitled "Method and Apparatus to Create Primordial Life from Inanimate Materials" that is substantially repeated in the application.

4 Claims, 10 Drawing Sheets

OTHER PUBLICATIONS

Deamer, et al., *Origins of Life, The Central Concepts*, Jones and Bartlett Publishers, Boston, MA, pp. 1–431, 1994.

de Duve, *Vital Dust*, Basic Books, A Division of Harper Collins Publishers, Inc., New York, NY, pp. 1–11, pp. 15–33, and pp. 341–362, 1995.

Dewan, *Essentials of Modern Open–Hole Log Interpretation*, PennWell Books, PennWell Publishing Company, Tulsa, OK, p. 230, 1983.

Editor, *A Dictionary of Biology*, Oxford University Press, New York, NY, Third Edition, 1996, pp. I–553.

Emiliani, *Planet Earth, Cosmology, Geology and the Evolution of Life and Environment*, Press Syndicate of University of Cambridge, Cambridge, Great Britain, pp. 128–154, 1995.

Ferris, et al., "The Effect of Clays on the Oligomerization of HCN", Journal of Molecular Evolution, vol. 13, pp. 317–330, 1979.

Ferris, et al., "Chemical Evolution 40. Clay–Mediated Oxidation of Diaminomaleonitrile",Journal of Molecular Evolution, vol. 18, pp. 304–309, 1982.

Ferris, et al., "HCN and Chemical Evolution: The Possible Role of Cyano Compounds in Prebiotic Synthesis", Tetrahedron, vol. 40, No. 7, pp. 1093–1120, 1984.

Ferris, et al., "The Investigation of the HCN Derivative Diiminosuccinonitrile as a Prebiotic Condensing Agent. The Formation of Phosphate Esters", Origins of Life, vol. 15, pp. 29–43, 1984.

Ferris, et al., "Clays as Prototypical Enzymes for the Prebiological Formation of Phosphate Esters", Origins of Life, vol. 16, pp. 473–474, 1986.

Ferris, et al., "The Adsorption and Reaction of Adenine Nucleotides on Montmorillonite", Origins of Life, vol. 17, pp. 69–84, 1986.

Ferris, et al., "Montmorillonite: A Multifunctional Mineral Catalyst for the Pebiological Formation of Phosphate Esters", Origins of Life, vol. 18, pp. 121–133, 1988, as reprinted on pp. 191–203 of Deamer, et al.

Ferris, et al., "Synthesis of Long Prebiotic Oligomers on Mineral Surfaces", Nature, vol. 381, pp. 59–61, May 2, 1996.

Gedulin, et al., "Sources and Geochemical Evolution of RNA Precursor Molecules: The Role of Phosphate", *Early Life on Earth*, Nobel Symposium No. 84, Columbia University Press, New York, NY, pp. 91–106, 1994.

Giacoletto, *Electronics Designers' Handbook, Second Edition*, McGraw–Hill Book Company, New York, NY, pp. 9–1 to 9–74, 1977.

Halliday, et al., *Physics, Parts I and II Combined*, John Wiley & Sons, New York, NY, Third Edition, pp. 650–674, 1978.

Harnwell, et al., *Experimental Atomic Physics*, McGraw–Hill Book Company, New York, NY, pp. 83–111, and pp. 308–323, 1933.

Kittel, *Introduction to Solid State Physics, Third Edition*, John Wiley & Sons, Inc., New York, NY, pp. 373–399, 1967.

Lahav, et al., "A Possible Role of Fluctuating Clay–Water Systems in the Production of Ordered Prebiotic Oligomers", Journal of Molecular Evolution, vol. 16, pp. 11–21, 1980.

Lee, *The Human Genome Project, Cracking the Genetic Code of Life*, Plenum Press, New York, NY, pp. 149–181, 1991.

Levine, et al., "The Prebiological Paleoatmosphere: Stability and Composition", Origins of Life, vol. 12, pp. 245–259, 1982.

Llewellyn–Jones, *Ionization and Breakdown in Gases*, Metheun & Co. Ltd., London, Great Britain, pp. 13–16, and pp. 46–76, 1957.

Loeb, *Basic Processes of Gaseous Electronics*, University of California Press, Berkeley, CA, pp. 597–611, pp. 646–660, and pp. 748–750, 1955.

Meek, *Electrical Breakdown of Gases*, Oxford at the Clarendon Press, Great Britain, pp. 83–100, pp. 223–250, and pp. 291–305, 1953.

Miller, "A Production of Amino Acids Under Possible Primative Earth Conditions", Science, vol., 117, pp. 528–529, 1953.

Miller, et al., "Organic Compound Synthesis on the Primitive Earth", Science, vol. 130, pp. 245–251, 1959.

Nicholl, *An Introduction to Genetic Engineering*, Studies in Biology Series, Cambridge University Press, Cambridge, United Kingdom, pp. 1–168, 1994.

Pace, "Origin of Life—Facing Up to the Physical Setting", Cell, vol. 65, No. 4, pp. 531–533, May 17, 1991.

Ponnamperuma, et al., "Clay and the Origin of Life", Origins of Life, vol. 12, No. 1, pp. 9–40, 1982.

Rao, et al., "Clays in Prebiological Chemistry", Journal of Molecular Evolution, vol. 15, No. 4, pp. 317–331, 1980.

Sleep, et al., "Annihilation of Ecosystems by Large Asteroid Impacts on the Early Earth", Nature, vol. 342, pp. 139–142, 1989.

Sogin, "The Origin of Eukaryotes and Evolution into Major Kingdoms", *Early Life on Earth*, Nobel Symposium No. 84, Columbia University Press, New York, NY, pp. 181–192, 1994.

Somerville, *The Electric Arc*, John Wiley & Sons Inc., New York, NY, pp. 1–9, 1959.

Stewart, "Nuclear Transplantation, An Udder Way of Making Lambs", Nature, vol., 385, pp. 769–771, Feb. 27, 1997.

Stryer, *Biochemistry*, W.H. Freeman and Company, New York, NY, Fourth Edition, pp. 3–16, pp. 75–94, and pp. 653–682, 1995.

Taubes, "Double Helix Does Chemistry At a Distance—But How?", Science, vol., 275, pp. 1420–1421, Mar. 7, 1997.

Urey, "On the Early Chemical History of the Earth and the Origin of Life", Proceedings of the National Academy of Sciences of the USA, vol. 38, No. 3, pp. 351–363, 1952.

von Engle, *Ionized Gases*, Oxford at the Clarendon Press, Great Britain, pp. 1–24, and pp. 194–196, 1955.

Watson, et al., *Molecular Biology of the Gene*, Benjamin/Cummings Publishing Company, Inc. Menlo Park, CA, Fourth Edition, pp. 962–1005, and pp. 1098–1163, 1987.

Westheimer, "Why Nature Chose Phosphates", Science, vol. 235, pp. 1173–1178, 1987.

Wilmut, et al., "Viable Offspring Derived from Fetal and Adult Mammalian Cells", Nature, vol., 385, pp. 810–813, Feb. 27, 1997.

Yamorgata et al., Origins Life, vol. 11, No.4, pp 317–320; abstract only, 1981.

Miller et al. (1959) Science, vol. 130, pp 245–251, No. 3370.

METHOD AND APPARATUS TO SYNTHESIZE DNA AND DNA-LIKE MOLECULAR STRUCTURES BY APPLYING ELECTRIC FIELDS TO GASEOUS MIXTURES OF CHEMICAL REACTANTS CONTAINING TEMPLATE PARTICULATE MATTER

Major portions of this application have been previously disclosed in U.S. Disclosure Document No. 412788 entitled "Method and Apparatus to Create Primordial Life from Inanimate Materials" that was recorded by the United States Patent and Trademark Office on the date of Feb. 10, 1997; which has invention disclosures that were "witnessed and understood" by four individuals respectively on May 23, 1996 and Jun. 3, 1996; and which has yet other invention disclosures that were "witnessed and understood" by three individuals on Sep. 15, 1996. This Disclosure Document is included herein in its entirety by reference that includes a total of 61 sheets of description and drawings which includes various draft versions of the Disclosure Document that were "witnessed and understood" by other individuals. The "final version" of the Disclosure Document includes 30 pages of text, 4 sheets of figures, and a total of 27 cited references which is only a portion of U.S. Disclosure Document No. 412788, and which is referenced as item (a) in the Feb. 10, 1997 transmittal letter to the USPTO for U.S. Disclosure Document No. 412788. That "final version" of the Disclosure Document might be studied by the interested reader first in sequence among the various separate documents comprising the entirety of U.S. Disclosure Document No. 412788.

BACKGROUND OF THE INVENTION

1. Field of the Invention

The field of the invention generally relates to methods to synthesize organic substances that include at least the step of applying an electric field to the initial chemical reactants. This step to synthesize organic substances may include the use of template particulate matter in gaseous mixtures of the initial chemical reactants. The field of the invention further relates to apparatus to make the organic substances that include at least one means of applying an electric field to the initial chemical reactants. The apparatus to make organic substances may provide template particulate matter in gaseous mixtures of the initial chemical reactants. The field of the invention specifically relates the synthesis of polymers from monomers; the synthesis of DNA and DNA-like molecular structures from nucleotides; and the synthesis of proteins from amino acids.

The field of this invention also relates to the synthesis primordial life from inanimate materials. The field of the invention further relates to using the methods and apparatus to make artificial life and to clone existing living organisms and to clone artificial organisms.

2. Description of the Prior Art

At the time of the filing of the application herein, applicant is unaware of any prior art that is relevant to the invention.

SUMMARY OF THE INVENTION

An object of the invention is to provide apparatus to synthesize organic substances that includes means of applying an electric field to the initial chemical reactants.

Another object of the invention is to provide apparatus to synthesize organic substances that includes means of applying an electric field to gaseous mixtures containing template particulate matter and the initial chemical reactants.

Yet another object of the invention is to provide methods to synthesize organic substances that include at least the step of applying an electric field to the initial chemical reactants.

Still another object of the invention is to provide methods to synthesize organic substances that include the step of applying an electric field to gaseous mixtures containing template particulate matter and the initial chemical reactants.

Another object of the invention is to provide methods and apparatus to synthesize polymers from monomers.

Still another object of the invention is to provide methods and apparatus to synthesize nucleotides from initial reactants including the appropriate sugars, phosphates, and bases.

Yet another object of the invention is to provide methods and apparatus to synthesize DNA and DNA-like molecular structures from nucleotides.

Still another object of the invention is to provide apparatus to synthesize DNA and DNA-like molecular structures that includes the means of mixing predetermined nucleotides and template particular matter together in a gaseous medium to form a gaseous mixture and means to generate and apply an electric field to the gaseous mixture to form the reaction products that include DNA and DNA-like molecular structures.

Another object of the invention is to provide methods to synthesize DNA and DNA-like molecular structures that include the step of mixing predetermined nucleotides and template particular matter together in a gaseous medium to form a gaseous mixture and applying an electric field to the gaseous mixture to form the reaction products that include DNA and DNA-like molecular structures.

Yet another object of the invention is to provide methods and apparatus to synthesize proteins from amino acids.

Still another object of the invention is to provide methods and apparatus to synthesize primordial life.

Yet another object of the invention is to provide methods and apparatus to synthesize primordial life from inanimate chemicals.

Another object of the invention is to provide methods and apparatus to make artificial life.

Yet another object of the invention is to provide methods and apparatus to make artificial life from inanimate chemicals.

And a final object of the invention is to provide methods and apparatus to clone living organisms.

DESCRIPTION OF THE PREFERRED EMBODIMENTS

The inventor initially began consideration of apparatus and methods of operation of that apparatus described in the following while performing fundamental research on the problem of the origin of life on Earth. The detailed step-by-step logic behind this assertion is provided by the above defined U.S. Disclosure Document No. 412788 entitled "Method and Apparatus to Create Primordial Life from Inanimate Materials". The following apparatus and methods of operation are described in that U.S. Disclosure Document, and relevant but truncated versions of the appropriate text are included below, although certain changes have been made to the wording.

Figure 1:
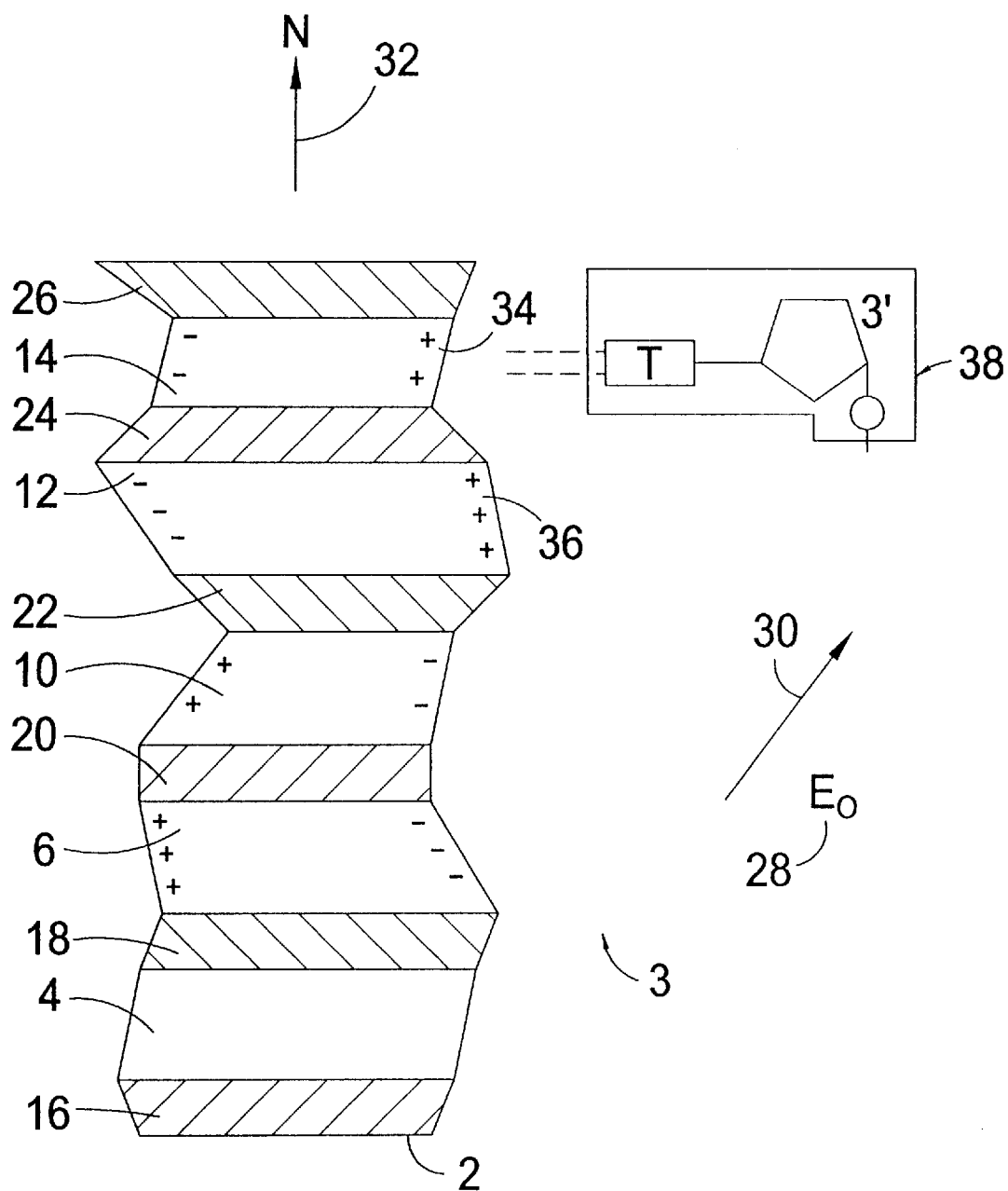
FIG. 1 shows a section view of a template particulate matter (that is an electrically layered material that is also dust particle), and a nucleotide in an applied electric field.

FIG. 1 shows a small shale particle 2 having laminated layers that is suspended in gaseous medium 3.

Dewan, 1983, page 230, points out that a shale "is a mixture of clay minerals and silt laid down in a very low-energy environment, principally by settlement from still water." He goes on to say: "The solids of a typical shale may consist of about 50% clay, 25% silica, 10% feldspar, 10% carbonates, 3% iron oxide, 1% organic material and 1% other material." Dewan also states "shale may also contain 2–40% water by volume". He further states: "Clay particles have a layered platelet structure. The crystalline platelets are very thin, 5–10 A, but may extend to about 10,000 A in length or width. They are stacked one above the other with spacing between them of 20–100 A. The clay particles are therefore extremely small—about 2 u in maximum dimension." (Here A stands for the angstrom unit and u stands for the micron unit.) The point is that shale is typically comprised of very thin laminated layers.

Relatively conducting layers 4, 6, 10, 12, and 14 are "sandwiched" between relatively insulating layers 16, 18, 20, 22, 24, and 26 of particle 2. Please note that relatively insulating layers 16, 20, and 24 and are made of different materials than layers 18, and 22 (as shown by different cross-hatching). Particle 2 is a particular example of template particulate matter—that is also called a dust particle for the purposes of this application. Template particulate matter with multiple layers is also called an electrically layered material ("ELM") for the purposes of this work. In general, it should be noted that template particulate matter may be any small dust like particle, although in several examples that follow, clay-containing or shale-like materials are prominently described.

An external electric field 28 is applied to particle 2 that has a direction defined in three dimensions by the vector 30. The external electric field 28 is also labeled with the legend "$E_o$" for clarity.

The particle 2 normally "tumbles" in the gaseous mixture under a number of different forces. The particle 2 in FIG. 1 has its normal axis 32 accidentally pointing in the "up direction". That normal axis 32 is also labeled with the legend "N" for clarity. Particle 2 is "frozen in time" for an instant in FIG. 1.

When the external electric field $E_o$ is applied to the particle, polarization charges appear on the surfaces of the particle. If the electric field points to the right for positive, it would normally be assumed that positive charges would build up on the surfaces to the right in FIG. 1. Such is the case at locations 34 and 36. However, it is known that under complex geometries and orientations, applied fields can generate polarization charges of any sign. See for example the figures in Kittel, 1967, page 381. The situation is further complicated by the fact that ferroelectrics exist with permanent dipole moments, ionic materials polarize, currents can flow in the particle, and a whole host of other complexities can exit. In any event, assume for the purposes herein that a material has been constructed which has the relative polarization charge distribution appearing on it shown by the "pluses" and "minuses" in FIG. 1 that are related to the magnitude and sign of the applied external electric field.

The applied electric field is influenced by many such particles in the gaseous mixture, each of which carries a separate overall charge, and other effects. Not mentioned so far is the fact that particle 2 can also carry a net charge represented by the symbol Q. That charge Q is not shown in FIG. 1 to prevent confusion with the polarization charges shown in FIG. 1. The net charge Q, the external electric field $E_o$, the dielectric and other electrical properties of the various layers, and the geometry of the particle result in polarization charge distributions, which in turn all act together with other particles present to produce a grand total electric field $E_t$ that is a vector, and that is a function of position. The vector $E_t$ is not shown for the purpose of clarity in FIG. 1. See Chapter 30 entitled "Capacitors and Dielectrics" of Halliday and Resnick, 1977, for an explanation of the difference between polarization charges and net external charges. For illustrative purposes in FIG. 1, assume that the net charge on the particle is a negative charge—i.e. it's value is—Q, where Q is a positive definite number.

Particle 2 in the external applied field has additional properties. Under the influence of the total electric field $E_t$, layer 14 has plus polarization charges induced on the right and negative polarization charges induced on the left. Under the influence of the total electric field $E_t$, layer 6 has plus polarization charges induced on the left and negative polarization charges induced on the right.

A nucleotide 38 is present in the gaseous medium in FIG. 1. The symbol for the nucleotide 38 uses symbols and nomenclature for nucleotides and DNA generally resembling those appearing in FIG. 1.2(a) on page 24, of Aldridge, 1996. The pentagonal structure is the sugar deoxyribose, the circle is for the phosphate group, T is for thymine, and the legend 3' specifies a direction that is defined in FIG. 1.2(a) of Aldridge, 1996. A simplified discussion of the basic structure of nucleotides is provided by Appendix 1 of Cairns-Smith, 1985. More detail on the structure of nucleotides within DNA is provided by Chapter 4 of Stryer, 1995, and in particular, see FIGS. 4-21. FIG. 4-21 in Stryer, 1995, shows how the phosphate group is appropriately incorporated into DNA.

Figure 2:
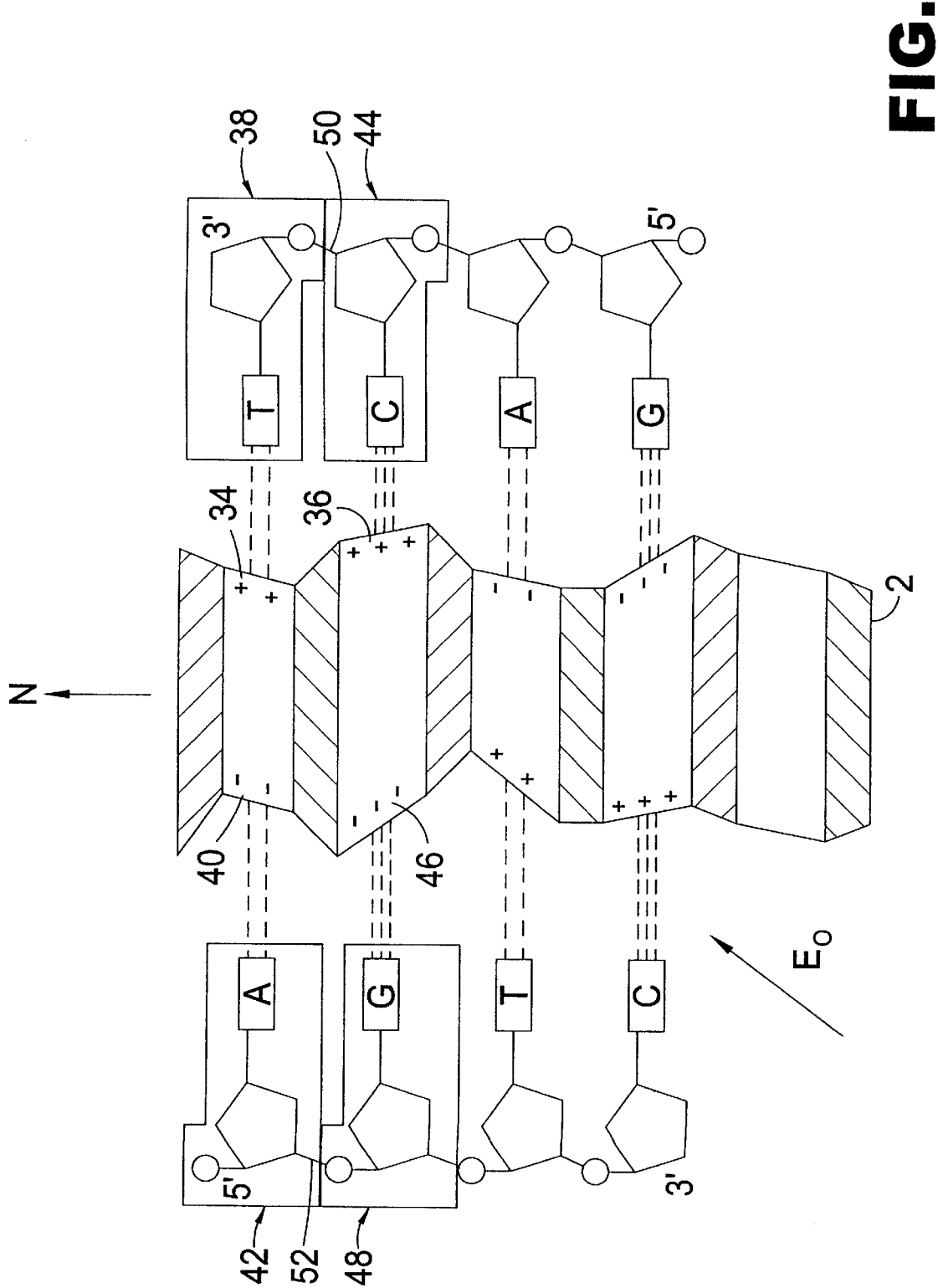
FIG. 2 shows a section view of a template particulate matter (that is an electrically layered material that is also a dust particle), and a portion of a DNA-like molecular structure forming on a dust particle.

FIG. 2.3(a) on page 12, Nicholl 1995, shows that Thymine is a hydrogen acceptor, i.e. it tends to bind to a relatively positively electrically charged region in simplistic terms. Also see Stryer, 1995, page 7, that defines "hydrogen donor" and "hydrogen acceptor" and which also further states: "The acceptor has a partial negative charge that attracts the hydrogen atom." Please also refer to FIG. 4-9 entitled "Model of an adenine-thymine base pair" and to FIG. 4-10 entitled "Model of guanine-cytosine base pair" on page 81, of Stryer, 1995. Two hydrogen bonds are in the process of forming between T and region 34 of the particle in FIG. 1.

FIG. 2 shows that T of nucleotide 38 has actually formed a double hydrogen bond between itself and region 34 (or it has formed a bond analogous to the double hydrogen bond for the purposes herein). Also shown in FIG. 2 are the following additional legends: A stands for adenine; G stands for guanine; C stands for cytosine; and the legend 5' specifies a direction that is defined in FIG. 1.2(a) of Aldridge, 1996.

In view of the above description and references, the appropriate sugar, phosphate, and base compositions of DNA and DNA-like molecular structures have been adequately defined for the purposes of this invention. Further, the appropriate sugar, phosphate, and base compositions of nucleotides comprising DNA and DNA-like molecular structures have been adequately defined for the purposes of this invention.

Please notice that because of the opposite signs of polarization charges induced within a particular given layer, that pairs of nucleotides which are complementary are naturally arranged on opposite sides of a given layer. This is an important point for the formation of DNA and DNA-like molecular structures. For the purpose of this invention, RNA, the different forms of RNA, and the various different geometric and configurational forms of DNA are all called herein DNA-like molecular structures. Region 40 is relatively electronegative because of the presence of negative polarization charges, so that A of nucleotide 42 tends to form two hydrogen bonds to region 40 of the particle. So, the layer defined by the medium joining regions 34 and 40 in FIG. 2 preferentially aligns A and T in a complementary fashion.

The phosphate ends of isolated nucleotides are known to carry a predominately negative net charge. See Westheimer, 1987, and Gedulin and Arrhenius, 1994. So, if the net charge on the particle 2 is—Q, then the phosphates would tend to "point away" from the net negative charge. However, the relative positive polarization charge in region 34 would tend to attract the T end of the nucleotide 38. Since A is complementary to T, then the relative negative polarization charge in region 40 would tend to attract the A end of nucleotide 42. Therefore, A would tend to be preferentially lined up with T.

(Please note that if the net charge on particle 2 were to be positive instead, then quite different effects would be produced, namely the phosphate ends of the nucleotides would tend to be attracted to the particle itself. Direct phosphate attachment would, of course, be useful for other purposes, including the preferential alignment of phosphates and sugars resulting in the formation the sugar-phosphate backbones of the DNA strands. Direct phosphate attachment would also be useful for the formation of the nucleotides themselves on yet other clay particles, or other particulate matter, from sources of the separate building blocks of the appropriate phosphates, sugars, and bases. That, of course, is another topic in itself that will be addressed below.

Similarly nucleotide 44 has C form a tripple hydrogen bond (or analogous bond) to region 36, and nucleotide 48 has G form a tripple hydrogen bond with region 46. Because of relative alignments, the sugar-phosphate bonds have in addition joined at locations 50 and 52 respectively to begin the sugar-phosphate backbones of a DNA-like molecular structure. In this way, a DNA-like molecular structure can be built up with complementary pairs of nucleotides forming on the electrically layered dust particle in a gaseous mixture.

Figure 3:
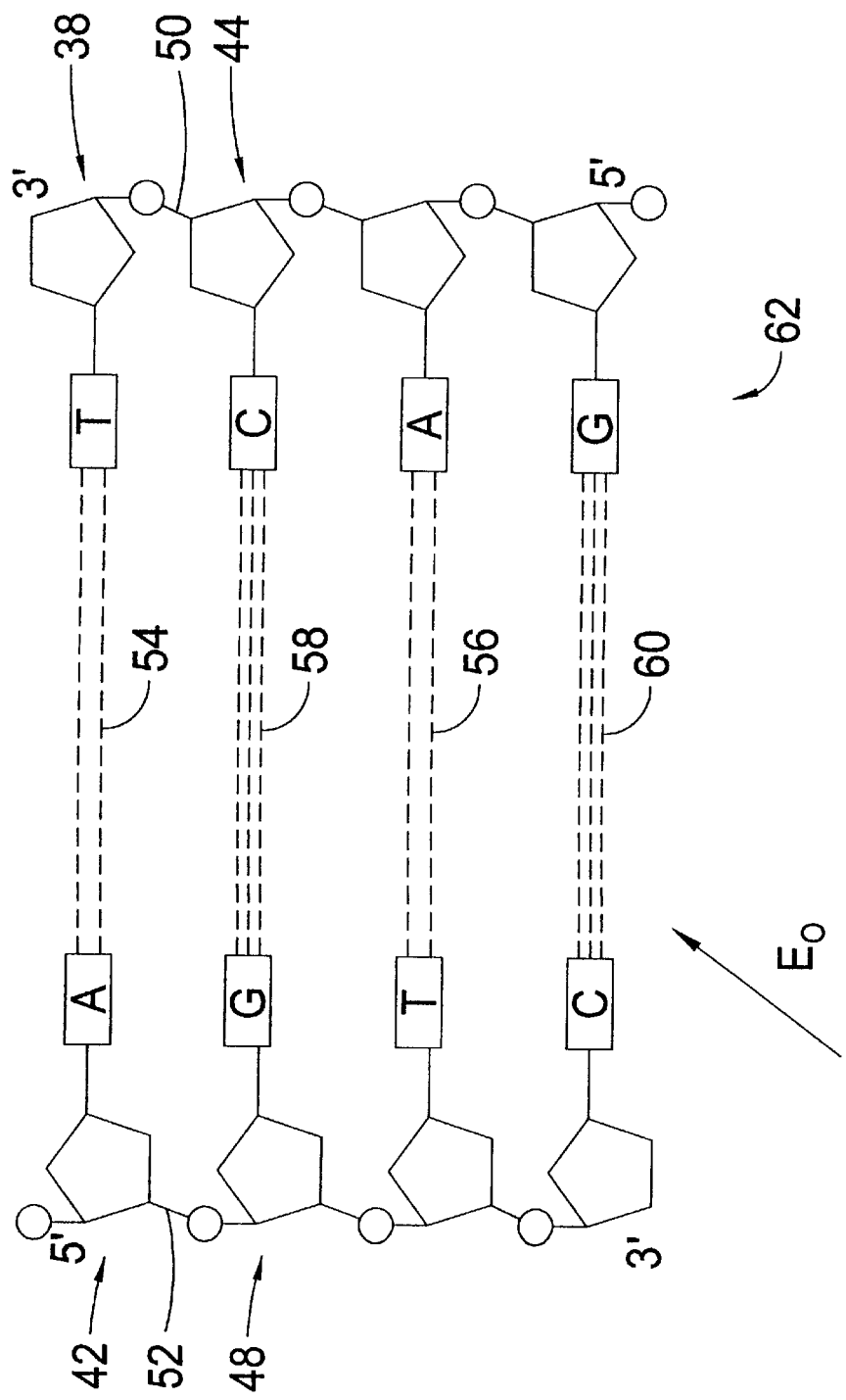
FIG. 3 shows the situation after the complementary base pairs in FIG. 2 have "jumped" in place forming a DNA-like molecular structure.

After aligning complementary pairs, there will be tendency for the complementary base pairs A-T and G-C to spontaneously "jump" together because this will be a lower energy situation. FIG. 3 shows the situation after the complementary base pairs in FIG. 2 have "jumped" in place.

In FIG. 3, particle 2 has disappeared, and double hydrogen bonds 54 have subsequently formed between A and T; double hydrogen bonds 56 have formed between T and A; triple hydrogen bonds 58 have formed by G and C; and triple hydrogen bonds 60 have formed between C and G. The formation of these respective double and triple hydrogen bonds have resulted in the DNA fragment 62 shown in FIG. 3. DNA fragment 62 is a DNA-like molecular structure for the purposes of this invention. The formation of the appropriate double and triple hydrogen bonds are equivalent to the statement that the complementary base pairs of the DNA-like molecular structure have "jumped" in place.

The double and triple hydrogen bonding process and the elimination of particle 2 as the template may be facilitated in a number of ways. Any water droplet surrounding a dust particle would tend to preferentially dissolve the dust particle thereby allowing the complementary base pairs to join. Perhaps acids present in the water droplet dissolve the particle. Perhaps the bases from the nucleotides dissolve a weakly acidic particle surrounded by a water droplet. Perhaps other liquids form around the dust particle to aid the spontaneous pairs A-T and C-G to "jump" together through the formation of the appropriate double and triple hydrogen bonds. Many mechanisms are possible.

After the dust particle has dissolved, or the bases have otherwise suitably formed the hydrogen bonds required, then a DNA-like molecular structure can emerge having characteristics similar to those shown in FIG. 2.3 and FIG. 2.4 of on pages 12 and 13 of Nicholl, 1995. Different artistic renditions of those drawings have been respectively provided herein, respectively in FIG. 4, FIG. 5, and in FIG. 6.

Figure 4:
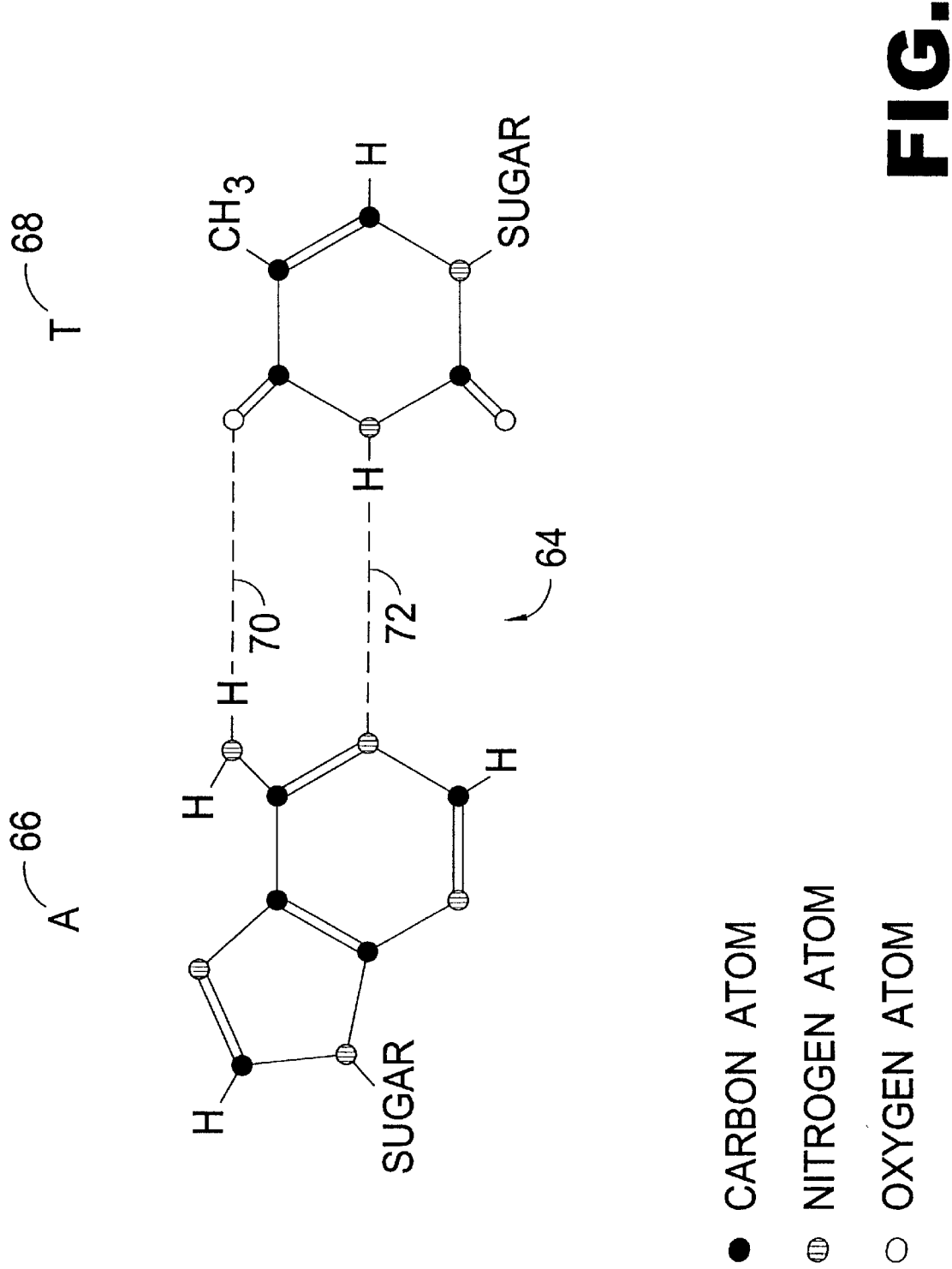
FIG. 4 shows the typical arrangement in DNA for an A-T base pair.

FIG. 4 shows the typical arrangement in DNA for an A-T base pair 64. In FIG. 4, adenine 66 is labeled with legend A and thymine 68 is labeled with legend T. Single hydrogen bond 70 and single hydrogen bond 72 have formed. Altogether, the A-T base pair requires a total of two separate hydrogen bonds. Any solid black dot in FIG. 4 is a carbon atom which is labeled with the legend "CARBON ATOM". Any large cross-hatched circle in FIG. 4 is a nitrogen atom which is labeled with the legend "NITROGEN ATOM". Other standard chemical symbols are used as following legends in FIG. 4: H for any hydrogen atom; O for any oxygen atom; $CH_3$ for a any carbon atom bonded to 3 hydrogen atoms; and a sugar molecule, generally standing for deoxyribose, that is labeled with the legend "SUGAR".

Figure 5:
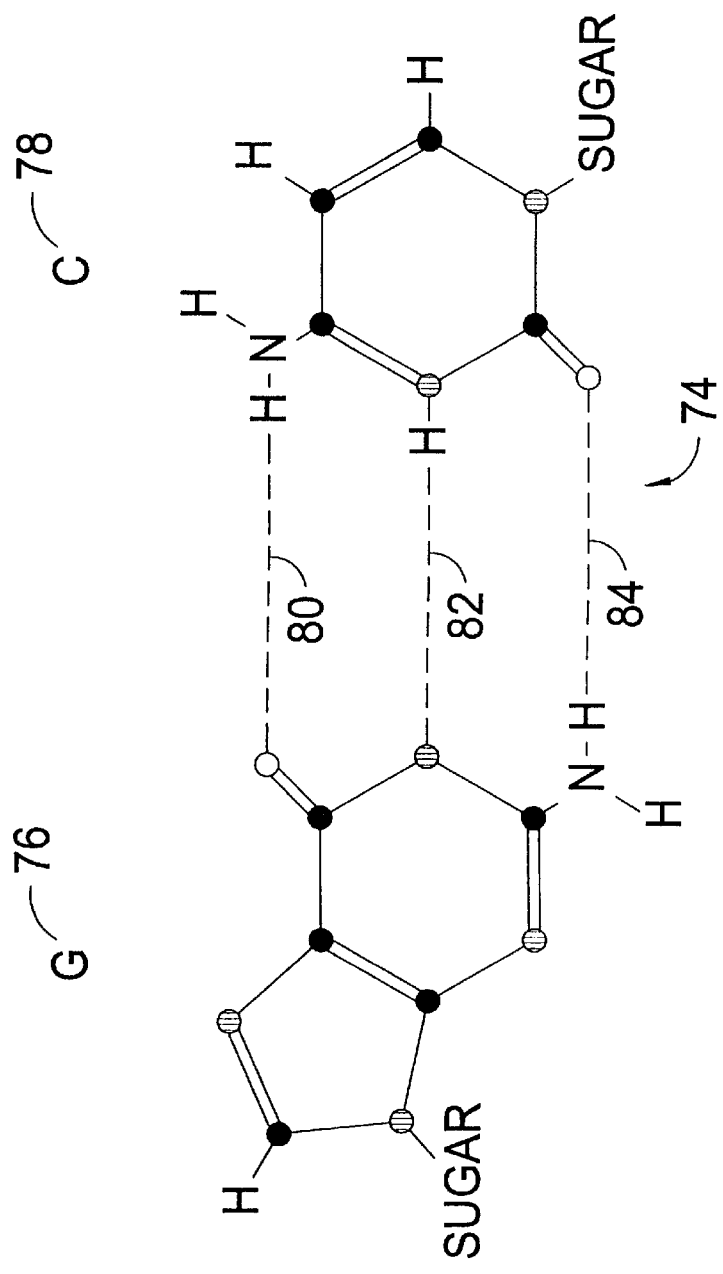
FIG. 5 shows the typical arrangement in DNA for an G-C base pair.

FIG. 5 shows the typical arrangement in DNA for a G-C base pair 74. In FIG. 5, guanine 76 labeled with legend G and cytosine 78 is labeled with legend C. Single hydrogen bond 80, single hydrogen bond 82, and single hydrogen bond 84 have formed. Altogether, the G-C base pair requires a total of three separate hydrogen bonds. The other legends used in FIG. 5 have been defined in FIG. 4.

Figure 6:
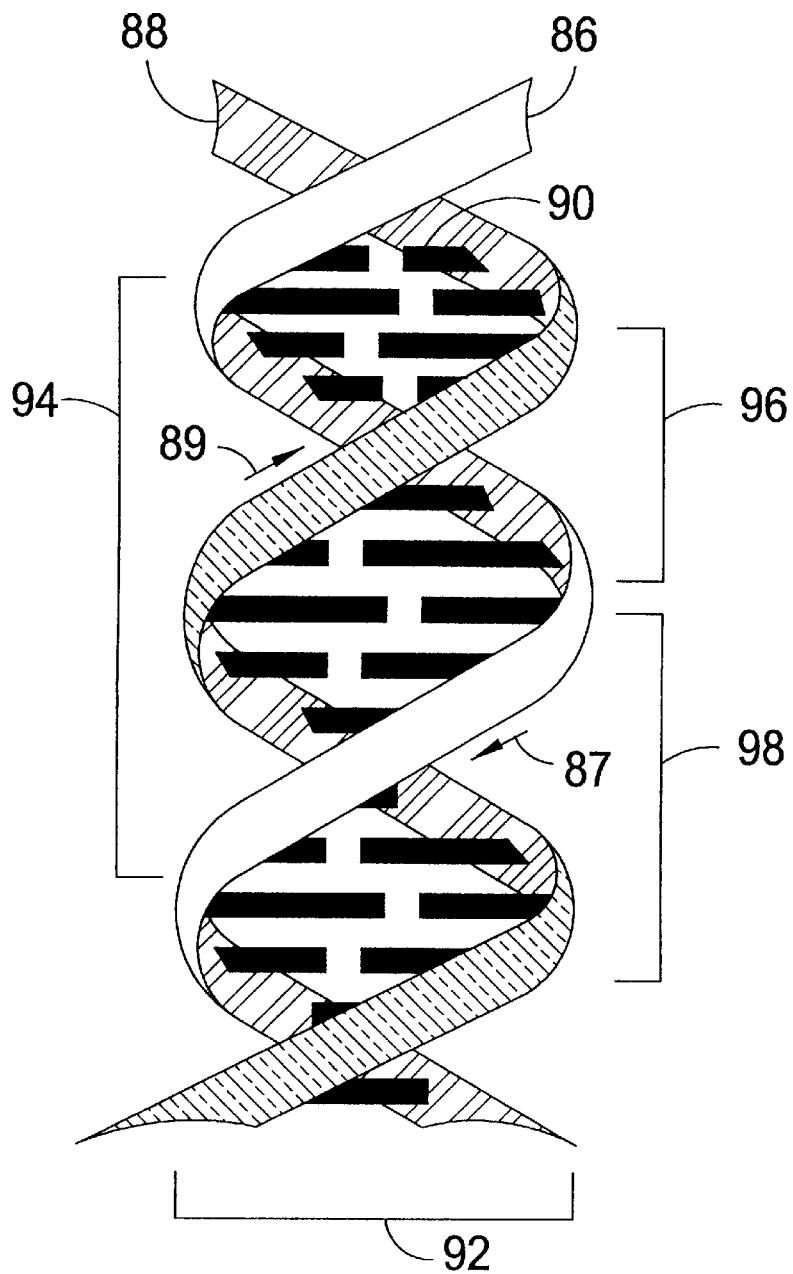
FIG. 6 shows the double helix of DNA that is in the beta-form.

FIG. 6 shows the double helix of DNA that is in the beta form. A first sugar-phosphate backbone 86 is oriented in a first direction noted by the downward pointing arrow 87. The first sugar-phosphate backbone 86 is one separate strand of DNA. The second sugar-phosphate backbone 88 is oriented in the opposite direction noted by the upward pointing arrow 89. The second sugar-phosphate backbone 88 is another separate strand of DNA. A typical base-pair 90 is shown joining the sugar-phosphate backbones together (that may be A-T, T-A, C-G, or G-C). The diameter 92 of the DNA is typically 20 nm across. The pitch of the DNA is about 3.4 nm with about 10 base pairs per 360 degree turn of the DNA. The DNA has a minor grove 96 and a major grove 98. This description and the related references adequately define for the purposes herein the meaning of the sugar-phosphate backbones of DNA that comprise the double-helix structure of DNA and DNA-like molecular structures.

Figure 7:
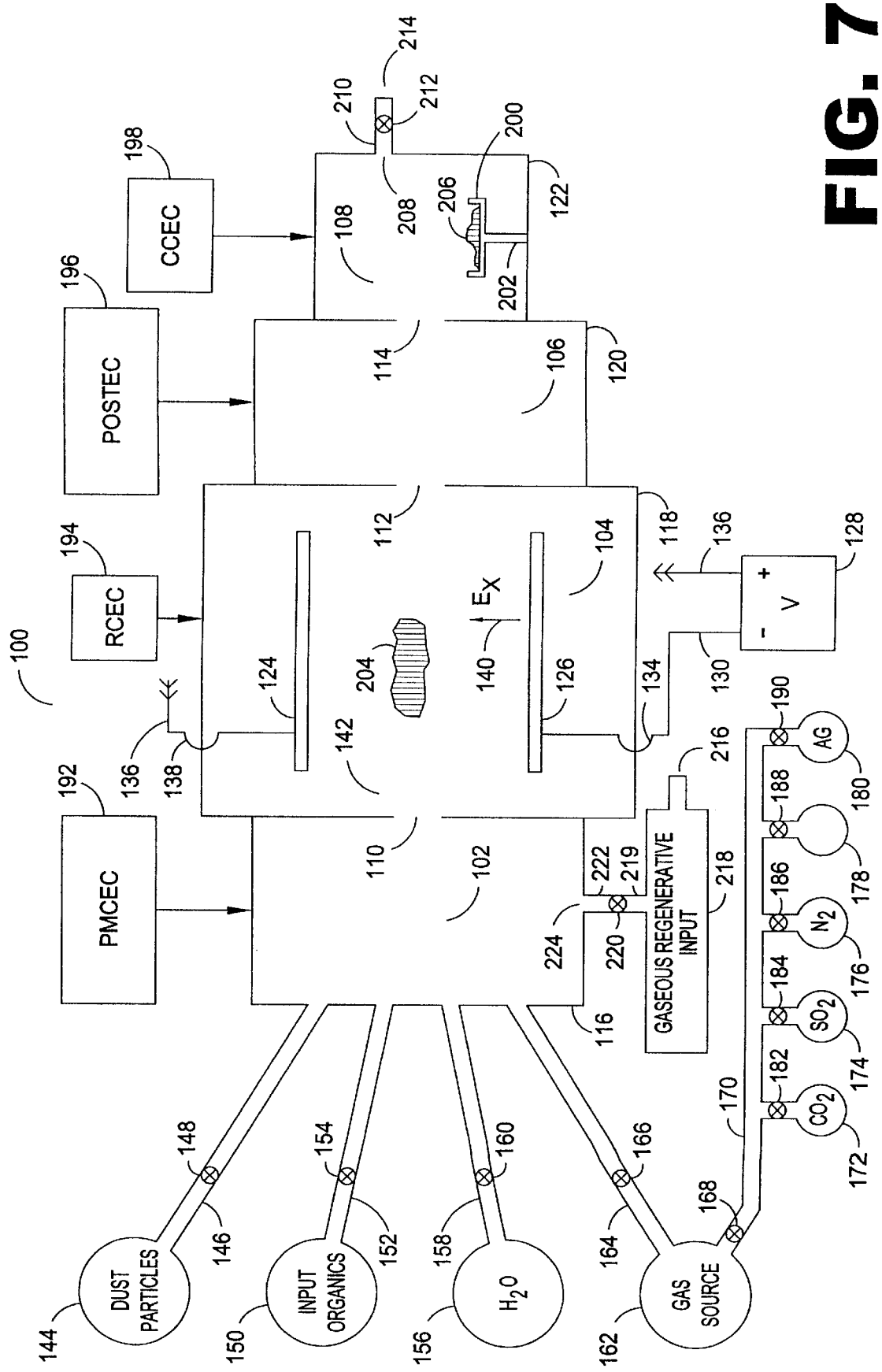
FIG. 7 is a diagram of the Electro-Particle Reactor (EPR).

Therefore, DNA and DNA-like molecular structures are made by mixing predetermined nucleotides and template particular matter together in a gaseous medium to form a gaseous mixture and by applying an electric field to said gaseous mixture to form the reaction products that include DNA and DNA-like molecular structures. FIG. 7 shows an apparatus that may be used to create DNA and DNA-like molecular structures. The apparatus shown in FIG. 7 may be used for many other purposes as well as explained later, but for the purposes of describing the working of the apparatus, the inventor will assume that it is used to make DNA and DNA-like molecular structures for what immediately follows.

FIG. 7 shows the "Electro-Particle Reactor" abbreviated as "EPR" that shows a preferred embodiment of the invention. The overall apparatus is labeled with the numeral 100. FIG. 7 shows a section view of the EPR.

The EPR 100 has a total of 4 main chambers, respectively labeled from left to right as 102, 104, 106, and 108. The pre-mixing chamber 102 of the EPR mixes various substances together under controlled circumstances. The reaction chamber 104 of the EPR produces the reactions under the influence of an electric field that is described below. The post-reaction chamber 106 of the EPR allows the reaction products to mix under controlled circumstances. The reactant catch chamber 108 is intended to accumulate the reaction products from the EPR.

Passage 110 connects the pre-mixing chamber 102 to the reaction chamber 104. Passage 112 connects the reaction chamber 104 to the post-reaction chamber 106. Passage 114 connects the post-reaction chamber 106 to the reactant catch chamber 108.

The pre-mixing changer 102 has wall 116. The reaction chamber 104 has wall 118. The post-reaction chamber 106 has wall 120. The reactant catch chamber 108 has wall 122. All the respective walls are vacuum tight, and have clean surfaces such as glass, fused silica, or type 316 stainless steel, etc.

Metal plates 124 and 126 in FIG. 7 form the plates of a capacitor within the reaction chamber 104. Capacitor plate 126 is connected to the negative output of voltage source 128 by wire 130 that passes through electrical feedthrough insulator 134. Capacitor plate 124 is connected to the positive output of voltage source 128 by wire 136 shown in broken format in FIG. 7 for the purpose of clarity. Wire 136 passes through electrical feedthrough insulator 138 to metal plate 124.

When a voltage difference V is applied to wires 130 and 136, there exists a voltage difference V between capacitor plates 124 and 126. Voltage source 128 is labeled with the legend V for the purposes of clarity. Voltage difference V between the capacitor plates 124 and 126 generates an applied external electric field 140 that is labeled with the legend $E_x$ in FIG. 7. This external electric field $E_x$ is generally caused to be a constant within the general region defined as 142 in FIG. 7. The length of each capacitor plate is L and their separation is D, although these dimensions are not shown in FIG. 7 for clarity. V can have both a D.C. value and an A.C. or any other time varying value suitable to generate any form of time varying electric field $E_x$ to produce the desired reaction products.

Element 144 is the dust particle source of the EPR. It supplies dust particles to pre-mixing chamber 102 through tube 146 that has stop-cock 148. The dust particle source 144 is capable of providing any predetermined size distribution of any type of particulate matter, at any predetermined temperature, at any predetermined pressure, in any type of gaseous or liquid medium. So, dust particle source 144 provides the basic source of particles to the EPR.

Dust particle source 144 is labeled with the legend "DUST PARTICLES" for clarity in FIG. 7. For example, the dust source provides any predetermined size distribution of particulate matter generally described as clay, shale, any type of mineral substance, or any artificially produced chemical compound that is particulate in nature. The particulate matter specifically includes layer silicates, kaolinite, dickite, halloysite, illites, smectities, zeolites, manganates, oxhydroxides, any type of mineral substance and any type of ELM described above. Virtually any substance is a candidate for the particulate matter including the following: (a) all such substances listed in standard chemical handbooks such as the "CRC Handbook of Chemistry and Physics", 61st Edition, the CRC Press, Boca Raton, Fla. and any updated versions thereof; (b) those substances listed in any of the standard lists of minerals occurring throughout the world; and (c) any reference on such chemical substances and minerals which are listed in current "Books in Print", Reed Reference Publishing Co., New Providence, N.J. (or its equivalent), entire copies of which are included herein in their entirety by reference.

In this particular case, a very early choice for particulate matter is montmorillonite. This has been shown to act as a catalyst for the formation of phosphate esters in certain laboratory conditions. For example, see Ferris, et. al., 1988, and Cowen, 1995, page 12, that states: ". . . nucleotides form faster in the presence of the clay mineral montmorillonite . . ." with respect to certain liquid chemical experiments.

The input organic material injector 150 provides predetermined organic materials to the pre-mixing chamber 102 through tube 152 that has stop-cock 154. In general, the input organic material injector 150 provides any predetermined distribution of organic materials of any type, at any predetermined pressure, in any type of gaseous or liquid medium. So, the input organic material injector provides the input source of organic material to the EPR.

The input organic material injector 150 is labeled with the legend "INPUT ORGANICS" for clarity in FIG. 7. In this particular case, to make DNA and DNA-like molecular structures, the starting organic material is a selection of the 4 different types of nucleotides. As explained earlier, the nucleotides have the structure of phosphate-sugar-base that is characteristic of DNA where the bases must be one of the following: A, T, C and G.

Water droplet source 156 provides water to the pre-mixing chamber 102 through tube 158 that has stop-cock 160. Water droplet source 156 provides water droplets in any particle size distribution, at any predetermined temperature distribution, at any predetermined pressure to the pre-mixing chamber 102. Therefore, the water droplet source has the capability of providing simultaneously any distribution of diameters of water droplets, any distribution of steam particles, and any distribution of ice crystals, or ice balls, to pre-mixing chamber 102. Water droplet source 156 is labeled with the legend "$H_2O$" in FIG. 7 for clarity.

The gas source 162 provides predetermined mixtures of gasses to pre-mixing chamber 102 through tube 164 that has stop-cock 166. Stop-cock 168 controls the entry of gases into gas source 162 from collection tube 170. Respective sources of pure gases 172, 174, 176, 178, etc. through 180

(in principle M sources of gases, where M can be any number) are supplied through respective stop-cocks 182, 184, 186, 188 and 190 to collection tube 170 in FIG. 7. Carbon dioxide, sulphur dioxide, and nitrogen gasses are respectively provided in separate gas sources 172, 174, and 176 that are labeled respectively with the legends $CO_2$, $SO_2$, and $N_2$ in FIG. 7 for clarity.

The overall environment of the pre-mixing chamber 102 is controlled by the pre-mixing chamber environmental control 192 that is labeled with legend PMCEC. This PMCEC controls the temperature and pressure within pre-mixing chamber and in addition, can provide any type of pre-determined additional energy sources to the pre-mixing chamber. For example, the PMCEC can provide simulations of lightning, cosmic rays, shock waves due to comets or meteors entering the Earth's atmosphere, any distribution of solar radiation, etc.

The overall environment of the reaction chamber 104 is controlled by reaction chamber environmental control 194 that is labeled with the legend RCEC. The RCEC controls the pressure and temperature of the reaction chamber 104, that in this mode of operation does not provide simulations of additional energy sources (although it could in principle, but that case is not shown in FIG. 7 for simplicity).

The overall environment of the post-reaction chamber 106 is controlled by the post-mixing chamber environmental control 196 labeled with the legend POSTEC to distinguish it from the prior acronym. The POSTEC controls the pressure and temperature within the post-mixing chamber and in addition, provides any type of pre-determined additional energy sources to the post-mixing chamber. For example, the POSTEC can provide simulations of lightning, cosmic rays, shock waves due to comets or meteors entering the Earth's atmosphere, any distribution of solar radiation, etc.

The overall environment of the catch chamber 108 is controlled by the catch chamber environmental control 198 labeled with the legend CCEC. The CCEC controls the temperature and pressure within the catch chamber and in addition, provides any type of pre-determined additional energy sources to the catch chamber. The CCEC can provide simulations of lightning, cosmic rays, shock waves due to comets or meteors entering the Earth's atmosphere, any distribution of solar radiation, etc.

The catch dish 200 is intended to "catch" a portion of the reaction products produced in the EPR. Catch dish 200 is supported by support 202. The CCEC provides independent temperature control of the catch dish 200 and also provides separate temperature control of the other region within the catch chamber 108.

To use the EPR to make DNA and DNA-like molecular structures, the following steps may be used. Dust particle source 144 is used to provide only small particles of montmorillonite. The input organics are chosen to be the four types of nucleotides typically comprising DNA. Steam is provided by water droplet source 156. The gasses chosen from gas source 162 are carbon dioxide, sulphur dioxide, and nitrogen in relative abundances from the present day Kilauea Volcano in Hawaii (see page 4 of Cowen, 1995).

The PMCEC is used to reduce the temperature of the mixtures in the pre-mixing chamber to 60 degrees F. and the pressure is chosen to be 1 atmosphere. The voltage V applied to plates 124 and 126 is chosen to be as large a D.C. voltage as possible, without causing electrical breakdown. Put succinctly in this embodiment, the intensity of the resulting electric field between the plates 124 and 126 is less than a threshold value to cause electrical breakdown in the gaseous mixture. The RCEC is chosen to provide 1 atmosphere of pressure and a temperature of 40 degrees F. The POSTEC is chosen to provide 1 atmosphere of pressure and a temperature of 35 degrees F. The CCEC is chosen to provide 1 atmosphere of pressure and a temperature of 32 degrees F.

A typical greatly enlarged particle of montmorillonite is shown as element 204 in the reaction chamber 104. It is acted upon by the external electric field $E_x$ in the presence of the four different nucleotides, water, and the gases introduced. A portion of the reaction products are deposited in a pile shown as numeral 206 in catch dish 200. Those particular reaction products are called the catch dish reactant products 206.

For one method of operating the EPR, proper functioning of the apparatus may be initially checked as follows. For a "first detailed list of all experimental parameters in the EPR", and for the voltage equal to some particular voltage V1, let the apparatus run for a particular length of time T1 (say 24 hours) and collect the reaction products. Call these the "reaction products 1, for V1, and for T1". Clean the apparatus.

Then, for the identical same "first detailed list of all experimental parameters in the EPR", but for the voltage equal to 0 volts, let the apparatus run for the same particular length of time T1 and collect the reaction products. Call these the "reaction products 2, for V0, and for T1".

Now chemically analyze the reaction products. Have fragments of DNA or DNA-like molecular structures been fabricated with V1? If so, the apparatus is operating properly. Were more reaction products produced with V1 than with V0? If so, the apparatus is again properly functioning in this one method of operation used here for explanatory purposes. However, this is just one preferred embodiment of the invention.

Put simply, if "reaction products 1, for V1, and for T1" has more DNA and DNA-like molecular structures than "reaction products 2, for V0, and for T1", then the apparatus is functioning properly using this particular method of operation. Many other methods of operation of the apparatus can also be described, but in the interests of brevity, this ends the description of the apparatus used to fabricate only DNA and DNA-like molecular structures.

The EPR may also be used to make polymers from monomers. Any type of suitable particulate template material may be chosen for the desired final chemical structure of the polymer. For example certain layered silicates may be used. In this case, dust particle source 144 is used to provide only small particles of layered silicates where the layering distance is suitable to hold monomers in place to make the polymer. The input organics are chosen to be the monomers of interest. Steam is provided by water droplet source 156. As an example, the gasses chosen from gas source 162 are carbon dioxide, sulphur dioxide, and nitrogen in relative abundances from the present day Kilauea Volcano in Hawaii (see page 4 of Cowen, 1995). However, this is just another preferred embodiment of the invention.

The EPR may also be used to make proteins from amino acids. Any type of suitable particulate template material may be chosen for the desired final chemical structure protein. For example certain layered organic-silicates may be used. In this case, dust particle source 144 is used to provide only small particles of layered organic-silicates where the layering distance is suitable to hold the amino acids in place to make the desired proteins. The input organics are chosen to be the amino acids of interest. Steam is provided by water droplet source 156. As an example, the gasses chosen from gas source 162 are carbon dioxide, sulphur dioxide, and nitrogen in relative abundances from the present day Kilauea Volcano in Hawaii (see page 4 of Cowen, 1995). However, this is just one more embodiment of the invention.

By analogy, it is now evident that the EPR may be used in general to make many different types of biologically active molecular structures from the predetermined input organics, by suitable choice of the template particulate matter supplied by the dust particle source, and by suitable choices of the water droplet source, the gas source, and the other parameters that may be controlled in the EPR. In fact, it is not only possible to make biologically active molecules with the EPR, but the EPR itself may be used to create primordial life as explained in the following.

The inventor's Disclosure Document No. 412788 entitled "Method and Apparatus to Create Primordial Life from Inanimate Materials" shows that the EPR can be used to create such primordial life. For the purposes herein, the creation of primordial life is equivalent to simulating any naturally occurring means capable of assembling and replicating DNA-like molecular structures which may take part in any type of naturally occurring evolutionary process that allows the DNA-like molecular structures to change in time. For the purposes herein, the creation of artificial life is equivalent to any artificial means capable of assembling and replicating DNA-like molecular structures which may take part in any type of artificial or actual evolutionary process that allows the DNA-like molecular structures to change in time. Put simply, primordial life is intended to simulate life as it evolved on Earth whereas artificial life is not necessarily intended to do so. With the current state of science, the inventor recognizes that it may not always be possible to draw a clear distinction between primordial life and artificial life. For the purposes in discussions involving primordial life and/or artificial life, DNA-like molecular structures include for the purposes of this invention any type of self-replicating molecular structure.

Before discussing how the EPR may be used to create primordial life, it is necessary to consider how life on earth might have logically formed. The inventor is indebted to Susan Aldridge for properly "setting the stage" for the following. The First, Second, and Third Stages are identified by my notations of "{First Stage}", "{Second Stage}", and "{Third Stage}" which have been respectively added to the following quote. Page 79 of Aldridge, 1996, states: "The origin of life is usually seen in three distinct stages. First {First Stage}, there has to be generation of basic organic building blocks such as nucleotides and amino acids. Next {Second Stage} comes assembly of these building blocks into functional polymers—DNA, RNA and proteins (this is generally reckoned to be the hardest thing to explain). Self-replication (nucleic acids) and catalysis (enzymes) are the chemical processes which got life going {Third Stage}."

Perhaps the First Stage above can be visualized as having been solved in-principle by the work of Stanley Miller and Harold Urey or otherwise solved by the use of the inventor's EPR as described above. See for example, Miller, 1953, and Miller and Urey, 1959.

The Third Stage above can be visualized as being solved in-principle in light of the following quote from Aldridge, 1996, page 82, as follows: "Once there were nucleic acids and proteins around, however primitive, they would have tended to reorganize themselves into cells. There is an explosion of interest today in the way big molecules sometimes self-organize into droplets and sheets. This behavior was noticed many years ago by Alexander Oparin, who demonstrated the formation of cell-like entities from the protein gelatin and gum arabic, a carbohydrate. These droplets, known as coacervates, let substances pass in and out of their membranes. If you put enzymes inside them, they will catalyze simple reactions. Eventually these first cells may have evolved into the first single-cell organism with a DNA genome. This is called the progenote and it is the ancestor of us all. It has left no trace, but with its emergence the stage was set for the story of the evolution of DNA to commence." The inventor also notes that lipid like materials are also ideally suited for encapsulating DNA and DNA-like materials.

The EPR may be used to create primordial life. One manner of doing so is as follows. Here, the dust particle source 144 provides particulate matter of montmorillonite. The input organic injector 150 provides a mixture of nucleotides and lipid materials. The water droplet sources provides water to the pre-mixing chamber 102 and the gas source 162 provides a mixture of carbon dioxide, sulphur dioxide, and nitrogen in relative abundances from the present day Kilauea Volcano in Hawaii (see page 4 of Cowen, 1995). Electrical discharges in the PMCEC and POSTEC are used to simulate the presence of thunderstorms in the Earth's atmosphere. The experimental parameters of the EPR are chosen to mimic those found in the early atmosphere of the Earth. The catch dish is subjected to the environmental controls of the CCEC. Please recall that the CCEC controls the temperature and pressure within the catch chamber and in addition, can provide any type of pre-determined additional energy sources to the catch chamber. The CCEC provides simulations of lightning, cosmic rays, shock waves due to comets or meteors entering the Earth's atmosphere, any distribution of solar radiation, etc. The CCEC provides any solution of any type required in the catch dish and provides any organic material of any additional type required in the catch dish. Primordial life is then formed in catch dish 200 by processes generally shown in FIGS. 1, 2, and 3 in this one more embodiment of the invention.

The EPR may be used to create artificial life. One manner of doing so is as follows. Here, the dust particle source 144 provides particulate matter of layered silicates. The input organic injector 150 provides a mixture of artificially prepared DNA-like molecular structures and lipid materials. (For example, the DNA-like molecular structures were prepared in another EPR that had suitably chosen input organics.) The water droplet source 156 provides water to the pre-mixing chamber 102 and the gas source 162 provides a mixture of carbon dioxide, sulphur dioxide, and nitrogen in relative abundances from the present day Kilauea Volcano in Hawaii (see page 4 of Cowen, 1995). The electrical discharges in the PMCEC and POSTEC are used to simulate the presence of thunderstorms in the Earth's atmosphere. The experimental parameters of the EPR are chosen to mimic those found in the early atmosphere of the Earth. The parameters of the CCEC are suitably chosen. The CCEC provides any solution of any type required in the catch dish and provides any organic material of any additional type required in the catch dish. Artificial life is then formed in catch dish 200 by processes analogous to those described in FIGS. 1, 2 and 3 in this particular embodiment of the invention.

Not described to this point are other aspects of the EPR in FIG. 7 so that multiple EPR's may be connected as follows. The EPR in FIG. 7 has an optional hole 208 in wall 122. If optional hole 208 is opened, it then connects to tube 210. Stop-cock 212 controls gaseous mixtures from escaping through the reactant catch chamber gaseous output 214.

If stop-cock 212 is open, then gaseous mixtures from the reactant catch chamber 108 can be recycled to the pre-mixing chamber 102 as follows. If stop-cock 212 is open, then the reactant catch chamber gaseous output 214 can be connected to input tube 216 of the gaseous regenerative input buffered pump unit 218 that is labeled with legend "GASEOUS REGENERATIVE INPUT" in FIG. 7. (The actual connection between the reactant catch chamber gaseous output 214 and the input tube 216 of the gaseous regenerative input buffered pump unit 218 is not shown for purposes of simplicity in FIG. 7). The gaseous regenerative input buffered pump unit 218 is used in part to control any pressure differential between the reactant catch chamber 108 and pre-mixing chamber 102. For brevity herein, the phrase "gaseous regenerative input buffered pump unit 218" shall be also called simply the "gaseous regenerative input 218" in the interests of brevity. The gaseous regenerative input 218 is connected to tube 219 that is in turn connected to stop-cock 220 that is in turn connected to tube 222 that is yet in turn connected to optional open hole 224 in wall 116 of the pre-mixing chamber 102. In this mode, the output from the reactant catch chamber gaseous output 214 is recycled into the gaseous regenerative input 218. In this particular mode of the invention, preferential chemical and physical reaction pathways may be made to self-amplify. By analogy to light-amplification-by-stimulated-emission characteristic of the optical laser, reaction products will then be "amplified" by this regenerative process so as to "run away" or self-amplify any preferred chemical and physical reaction pathways.

Figure 8:
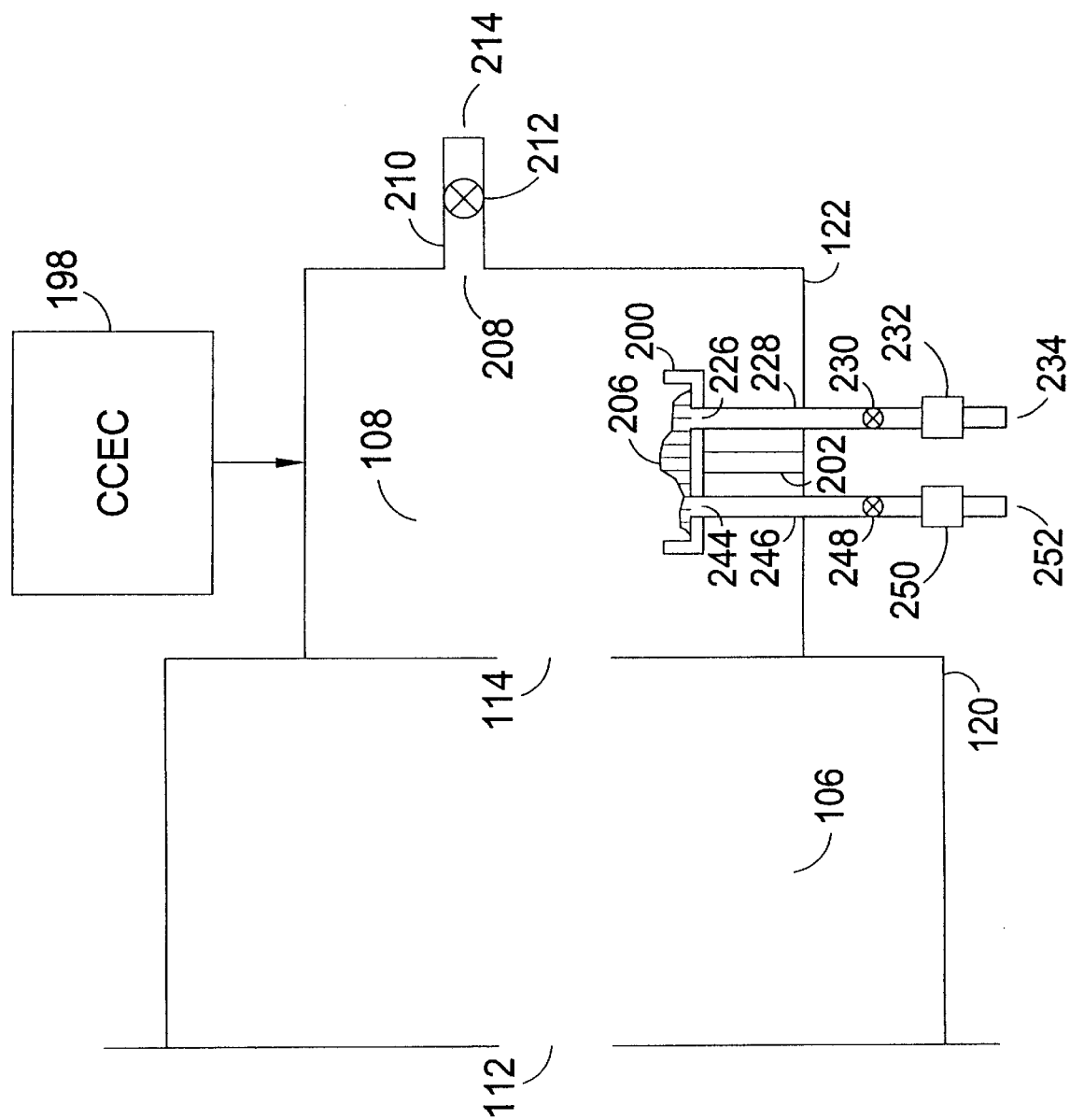
FIG. 8 shows an expanded view of the reactant catch chamber 108 from FIG. 7.

FIG. 7 does not show certain detail involving inputs and outputs from the catch dish 200 for reasons of simplicity. That detail is shown in FIG. 8. FIG. 8 shows an enlarged section view of catch chamber 108 and catch dish 200. Numerals 106, 108, 112, 114, 198, 200, and 214 have already been defined.

FIG. 8 also shows an output from catch dish 200. Optional hole 226 in catch dish 200 is connected to tube 228 that is in turn connected to stop-cock 230 that is in turn connected to catch dish output buffer pump 232 that provides the catch dish output 234. The catch dish output buffer pump 232 is used to compensate for any pressure differences between the existing pressure on the catch dish reactant products 206 located within the catch dish and the pressure existing in any destination chamber for those catch dish reactant products. In FIG. 8, the inventor has skipped numerals 235 through 243.

FIG. 8 also shows an input to catch dish 200. Optional hole 244 in catch dish 200 is connected to tube 246 that is in turn connected to stop-cock 248 that is in turn connected to catch dish input buffer pump 250 that takes the catch dish regenerative input 252 and pumps it to the interior of catch dish 200.

Catch dish output 234 and catch dish regenerative input 252 are used to connect many EPR's together. In principle, many EPR's may be sequentially connected together. Consider the case of n such EPR's lined up sequentially. Each would have a separate reactant catch chamber gaseous output (j), a gaseous regenerative input (j), a catch dish output (j) and a catch dish regenerative input (j). Here, j runs from 1, 2, . . . , n-1, n. Any reactant catch chamber gaseous output (j) may be connected to any other, or to any number (or to all) of the other gaseous regenerative inputs 1, 2, . . . n-1, n. Any catch dish output (j) may be connected to any other, or to any number of (or to all) of the other catch dish regenerative inputs 1, 2, . . . n-1, n. Each one of these individual EPR's have their own separate respective input dust particle source (j), input organic injector (j), water droplet source (j), and gas source (j).

Figure 9:
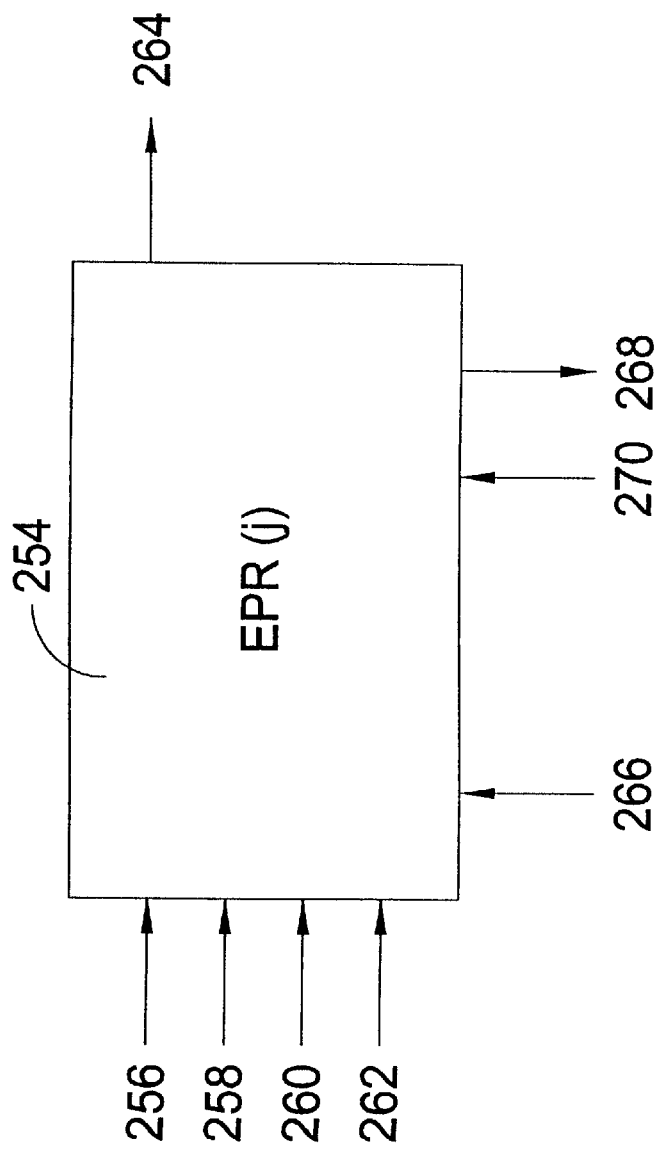
FIG. 9 shows a "jth" EPR called EPR(J).

A particular EPR, number j, is shown in FIG. 9 that is labeled with legend "EPR (j)". It is labeled with the numeral 254. Input dust particle source (j) labeled with numeral 256, input organic injector (j) labeled with numeral 258, water droplet source (j) labeled with numeral 260, gas source (j) labeled with numeral 262, reactant catch chamber gaseous output (j) labeled with numeral 264, gaseous regenerative input (j) labeled with numeral 266, catch dish output (j) labeled with numeral 268, and catch dish regenerative input (j) labeled with numeral 270 are used to connect to other EPR's as desired. In practice, n of such units may be hooked together to form an overall functional product.

For example in yet another embodiment of the invention, a first EPR may be used to create the building blocks of nucleotides as stated above. Then a second EPR may be used to assemble those nucleotides from the building blocks. Then a third EPR may be used to assemble those nucleotides into DNA. Then a fourth EPR may be used to place lipids or other organic material around the DNA to make primordial life. A fifth EPR may be used to make evolutionary changes in that primordial life by radiation or other environmental effects produced in the fourth EPR's pre-mixing chamber, as just one example. In the end, a succession of EPR's may be used to create primordial life and evolutionary changes in that primordial life from a series of input chemicals. It may turn out that the dust particle injector is of critical importance in only the first and second EPR. In that case, the lipids themselves would replace the dust particles in the third EPR to create primordial life that is consistent with operation of a succession of EPR's.

Figure 10:
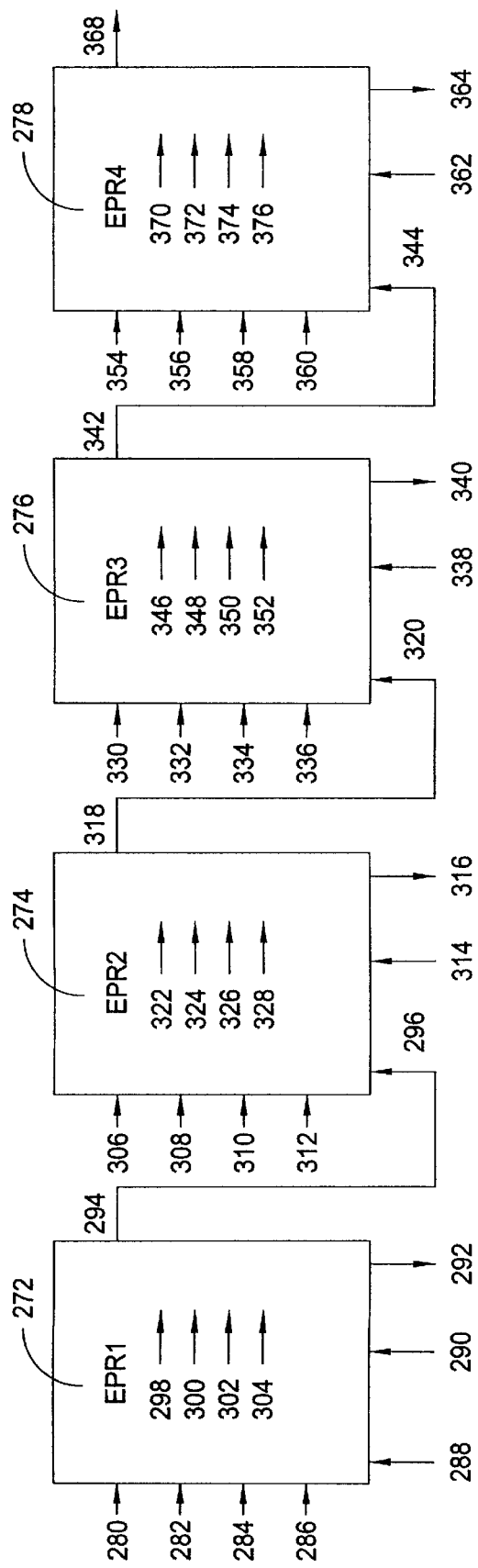
FIG. 10 shows four each EPR's in row: EPR 1, EPR 2, EPR 3 and EPR 4.

In this particular embodiment of the invention, a succession of 4 EPR's is shown in FIG. 10 to make primordial life. Element 272 is EPR 1. Element 274 is EPR 2. Element 276 is EPR 3. Element 278 is EPR 4. The purpose of EPR 1 is to create the required phosphates, sugars, A, T, G, and C which are the individual building blocks of the nucleotides. The purpose of EPR 2 is to actually assemble those building blocks into nucleotides. The purpose of EPR 3 is to assemble those nucleotides into DNA and/or DNA-like molecular structures. The purpose of EPR 4 is to place lipids or other organic material around the DNA or DNA-like molecular structures to make primordial life. It is now appropriate to go through this process of making primordial life step-by-step.

The purpose of EPR 1 in FIG. 10 is to make the building blocks for nucleotides that include the required phosphates, sugars, and the bases A, G, T and C, all of which have been adequately described above. The introduction of layered silicates by the dust particle source 280 of EPR 1, or other suitable template particulate matter, act as catalysts to make the building blocks of nucleotides more rapidly than would otherwise be the case. The input organic injector 282 of EPR 1 is chosen to provide inputs of only those elementary substances deemed present in the early atmosphere of the Earth. Water droplet source 284 of EPR 1 provides water droplets in the type and distribution of those found in the early atmosphere of Earth. Gas source 286 of EPR 1 provides those gases deemed to be present in the early atmosphere of the Earth. In the case of EPR 1, the gaseous regenerative input 288 of EPR 1 and the catch dish regenerative input 290 of EPR 1 are not used. The catch dish output 292 of EPR 1 is used to monitor the efficiency of making the required building blocks of the nucleotides. The reactant catch chamber gaseous output 294 of EPR 1 is connected to the gaseous regenerative input 296 of EPR 2 for further processing. The PMCEC of EPR 1 that is element 298, the RCEC of EPR 1 that is element 300, the POSTEC of EPR 1 that is element 302, and the CCEC of EPR 1 that is element 304 are set to produce optimum production of the building blocks of the nucleotides. For example, electric discharges resembling the effects of lightning in the early Earth's atmosphere are provided by elements 298 and 302. Elements 298, 300, 302, and 304 are chosen to provide the environmental conditions deemed appropriate for the early atmosphere of the Earth. Therefore, EPR 1 makes the building blocks of the nucleotides including the appropriate phosphates, sugars, A, G, T, and C that are injected into the gaseous regenerative input 296 of EPR 2 for further processing.

The last paragraph states in part: "Water droplet source 284 of EPR 1 provides water droplets in the type and distribution of those found in the early atmosphere of Earth. Gas source 286 of EPR 1 provides those gases deemed to be present in the early atmosphere of the Earth." For the purposes herein, the water droplet source and gas source for EPR 1 may be initially adjusted to mimic the abundances of water and gases in relative abundances from the present day Kilauea Volcano in Hawaii (see page 4 of Cowen, 1995). Similar cements apply to the following.

The purpose of EPR 2 in FIG. 10 is to make the nucleotides themselves that are used in a later step to make the phosphate-sugar-base structures used by DNA and DNA-like molecular structures where the bases are A, G, T and C. Dust particle source 306 of EPR 2 provides a suitable particle distribution of montmorillonite as the template particulate matter. The input organic injector 308 of EPR 2 is chosen to provide inputs of only those elementary substances deemed present in the early atmosphere of the Earth. Water droplet source 310 of EPR 2 provides water droplets in the type and distribution of those found in the early atmosphere of Earth. Gas source 312 of EPR 2 provides those gases deemed to be present in the early atmosphere of the Earth. The catch dish regenerative input 314 of EPR 2 is not used. The catch dish output 316 of EPR 2 is used to monitor the efficiency of making the required nucleotides. The reactant catch chamber gaseous output 318 of EPR 2 is connected to the gaseous regenerative input 320 of EPR 3 for further processing. The PMCEC of EPR 2 that is element 322, the RCEC of EPR 2 that is element 324, the POSTEC of EPR 2 that is element 326, and the CCEC of EPR 2 that is element 328, are set to produce optimum production of the nucleotides. Elements 322, 324, 326, and 328 are chosen to provide the environmental conditions deemed appropriate for the early atmosphere of the Earth. Therefore, EPR 2 makes the nucleotides having bases of the four different types: A, G, T and C that are injected into the gaseous regenerative input 320 of EPR 3.

The purpose of EPR 3 in FIG. 10 is to make DNA and DNA-like molecular structures from nucleotides having bases of A, G, T, and C. Dust particle source 330 of EPR 3 provides a suitable particle distribution of montmorillonite as the template particulate matter. The input organic injector 332 of EPR 3 is chosen to provide inputs of only those elementary substances deemed present in the early atmosphere of the Earth. Water droplet source 334 of EPR 3 provides water droplets in the type and distribution of those found in the early atmosphere of Earth. Gas source 336 of EPR 3 provides those gases deemed to be present in the early atmosphere of the Earth. (See the following embodiments for more on this point.) The catch dish regenerative input 338 of EPR 3 is not necessarily used, although fluids could be injected here to preserve any DNA or DNA-like molecular structures produced. The catch dish output 340 of EPR 3 is used to monitor the efficiency of making the required DNA and DNA-like molecular structures. The reactant catch chamber gaseous output 342 of EPR 3 is connected to the gaseous regenerative input 344 of EPR 4 for further processing. The PMCEC of EPR 3 that is element 346, the RCEC of EPR 3 that is element 348, the POSTEC of EPR 3 that is element 350, and the CCEC of EPR 3 that is element 352 are set to produce optimum production of DNA and DNA-like molecular structures. Elements 346, 348, 350, and 352 are chosen to provide the environmental conditions deemed appropriate for the early atmosphere of the Earth. Therefore, EPR 3 makes the DNA and DNA-like molecular structures that are injected into gaseous regenerative input 344 of EPR 4.

The purpose of EPR 4 in FIG. 10 is to make primordial life. Dust particle source 354 of EPR 4 provides a suitable particle distribution of montmorillonite as the template particulate matter. The input organic injector 356 of EPR 4 is chosen to provide a source of lipids or other organic material to surround the DNA and DNA-like molecular structures to make primordial life. The input organic injector 356 of EPR 4 also provides inputs of those elementary substances deemed present in the early atmosphere of the Earth as defined in the many references cited below. Water droplet source 358 of EPR 4 provides water droplets in the type and distribution of those found in the early atmosphere of the Earth. Gas source 360 of EPR 4 provides those gases deemed to be present in the early atmosphere of the Earth. The catch dish regenerative input 362 of EPR 4 is not necessarily used, but fluids can be injected here to preserve any primordial life produced (or it can be used for other purposes in other embodiments of the invention to create artificial life as fully described below). The catch dish output 364 of EPR 4 is used to monitor the efficiency of making primordial life. The reactant catch chamber gaseous output 368 of EPR 4 provides primordial life that is in particulate form. The PMCEC of EPR 4 that is element 370, the RCEC of EPR 4 that is element 372, the POSTEC of EPR 4 that is element 374, and the CCEC of EPR 4 that is element 376 are set to optimize production of primordial life. Elements 370, 372, 374, and 376 are chosen to provide the environmental conditions deemed appropriate for the early atmosphere of the Earth. Therefore, EPR 4 makes the final primordial life, where primordial life has already been defined previously.

In other preferred embodiments of the invention, the reactant catch chamber gaseous output 368 of EPR 4 can be connected to yet other EPR's to simulate the action of evolution on the primordial life as is now evident from the disclosure here. The respective environmental controls of the EPR's would be suitably adjusted to provide simulations of cosmic rays, lightning, ultra-violet rays, charged particle bombardment, pressure waves, etc. The final outputs of those EPR's include chemical components useful to the biochemical industry.

Artificial life was defined earlier. Artificial life may be produced in an analogous series of steps as set forth in FIG. 10 by using EPR 1, EPR 2, EPR 3, and EPR 4. To make artificial life, EPR 1, EPR 2, and EPR 3 are initially operated in manners described above. However, radically different steps may be taken involving the operation of EPR 4 to make certain forms of artificial life. Various organic and biological materials may be injected into catch dish regenerative input 362 of EPR 4. In one method of operation in one embodiment of the invention, actual biological cells are introduced into the catch dish regenerative input 362.

The purpose of EPR 3 is to provide DNA (and DNA-like molecular structures) to EPR 4. If a biological cell that has had its DNA first removed is inserted into catch dish regenerative input 362, then the DNA from EPR 3 may be used to combine with the cell having no DNA in it. Call the cell with no DNA in it a "negative cell". Then the DNA from EPR 3 can be processed in such a manner to enter into the negative cell within the catch dish within EPR 4. Then the cell having the DNA from EPR 3 can be grown in culture.

In yet another method, the negative cell with the DNA from EPR 3 can be joined with an unfertilized egg of a mammal that has had its nucleus removed that is called a negative egg herein. If the negative cell with the DNA from EPR 3 is put into the catch dish of EPR 4 with a negative egg, then the catch chamber environmental control (CCEC) 376 of EPR 4 may be used to physically join the cells in the catch dish. Methods of joining those cells in the catch dish include at least the following methods. The negative cell with the DNA from EPR 3 can be jointed with a negative egg by pressure waves from the CCEC. The negative cell with the DNA from EPR 3 can be joined with a negative egg by electric fields provided by the CCEC. The negative cell with the DNA from EPR 3 can be joined with a negative egg by magnetic fields provided by the CCEC. The negative cell with the DNA from EPR 3 can be joined with a negative egg by electric current provided by the CCEC. The negative cell with the DNA from EPR 3 can be joined with a negative egg by shock waves provided by the CCEC. The negative cell with the DNA from EPR 3 can be joined with a negative egg by ultra violet light provided by the CCEC. The negative cell with the DNA from EPR 3 can be joined with a negative egg by gamma rays provided by the CCEC. The negative cell with the DNA from EPR 3 can be joined with a negative egg by neutron bombardment provided by the CCEC. The negative cell with the DNA from EPR 3 can be joined with a negative egg by electron bombardment provided by the CCEC. The negative cell with the DNA from EPR 3 can be joined with a negative egg by elementary particle bombardment of any type provided by the CCEC. The negative cell with the DNA from EPR 3 can be joined with a negative egg by mechanical stirring provided by the CCEC. The negative cell with the DNA from EPR 3 can be joined with a negative egg by one or more laser-beams provided by the CCEC. For the purposes of this disclosure a negative cell is a cell with its nucleus removed, otherwise called an enucleated cell. For the purposes of this disclosure a negative egg is an egg with its nucleus removed, otherwise called an enucleated egg. Otherwise typical methods used in the industry and suitable fluids to preserve artificial life so produced would be injected into the catch dish regenerative input 362 of EPR 4 as described in the following references that are included herein in their entirety: Stewart, 1997; Wilmut, et. al., 1997; all of the references cited in Wilmut, et. al, 1997; Campbell, et. al., 1996; and Glass, 1993, in particular including Chapter 19 entitled "In Vitro Fertilization".

The inventor has been concerned with the question of how life originated on the Earth as set forth in the U.S. Disclosure Document No. 412788 entitled "Method and Apparatus to Create Primordial Life from Inanimate Materials". The suitable production of artificial life using negative eggs of the type described above may in fact speed this process by working "backward" by first substituting the original egg's DNA with DNA created by EPR 3.

The above methods are useful for other purposes such as for cloning. A somatic cell generally relates to all the cells of an animal (or plant) other than the reproductive cells of the animal (or plant). An enucleated egg has been defined above. Wilmut, et. al. 1997, showed that using an electric current to fuse a somatic cell from the utter of a ewe with an enucleated egg from an early sheep embryo is useful for the purposes of cloning sheep. The methods mentioned in the previous paragraph are also be useful for such cloning of animals. For example, a somatic cell can be joined with an enucleated egg by pressure waves to clone the source of the somatic cell. A somatic cell can be joined with an enucleated egg by application of electric fields to clone the source of the somatic cell. (Both static and pulsed electric fields may be used for this purpose.) A somatic cell can be joined with an enucleated egg by application of magnetic fields to clone the source of the somatic cell. (Both static and pulsed magnetic fields may be used for this purpose). A somatic cell can be joined with an enucleated egg by shock waves to clone the source of the somatic cell. A somatic cell can be joined with an enucleated egg by ultra violet light to clone the source of the somatic cell. A somatic cell can be joined with an enucleated egg by gamma rays to clone the source of the somatic cell. A somatic cell can be joined with an enucleated egg by neutron bombardment to clone the source of the somatic cell. A somatic cell can be joined with an enucleated egg by electron bombardment to clone the source of the somatic cell. A somatic cell can be joined with an enucleated egg by bombardment by elementary particles of any type, such as by protons, to clone the source of the somatic cell. A somatic cell can be joined with an enucleated egg by mechanical stirring to clone the source of the somatic cell. A somatic cell can be jointed with an enucleated egg by application of a laser beam to clone the source of the somatic cell. In this paragraph, the source of the somatic cell is meant to mean the animal from which the somatic cell was removed. However, it is evident from the above description that somatic cells from plants can be suitably joined to appropriately enucleated reproductive cells of plants for the purposes of cloning as well. See for example Chapter 27 entitled "Plant Reproduction and Development" of Audesirk and Audesirk, 1993. The above methods of joining somatic cells can be further generalized to fuse appropriately chosen prokaryotic cells as well.

It should also be noted that particle 2 in FIG. 1 has been described in various embodiments as an example of template particulate matter, as an example of a dust particle, which in some embodiments is also an example of an electrically layered material (ELM). As is now evident from the disclosure, in some embodiments of the invention these materials act essentially as catalysts. According to "A Dictionary of Biology", 1996, that is listed in the below defined references, a catalyst is "A substance that increases the rate of a chemical reaction without itself undergoing any permanent chemical change. The catalyst provides an alternative pathway by which the reaction can proceed, in which the *activiation energy is lower." For several particular embodiments herein, the phrases template particulate matter, dust particle, and catalyst may all be used interchangeably. An electrically layered material may in certain embodiments also be an example of a catalyst as used herein. However, in yet other embodiments of the invention, it is contemplated that the template particulate matter, dust particle, or electrically layered material may actually contribute chemical components to the final reaction products. In such cases, such template particulate matter, dust particle, or ELM would not be classified as a catalyst in view of the above definition. Accordingly, the inventor has used the term "catalyst" sparingly in the above specification because of its precise meaning.

It is also evident from the above disclosure that the DNA and DNA-like molecular structures made by an Electro-Particle Reactor (EPR) would be useful for the purposes of information storage and for computation with any computers using DNA-like molecular structures for memories.

It is also evident from the above disclosure that template particulate matter may also be used to investigate the electrical characteristics of DNA and DNA-like molecular structures. For example, see Taubes, 1997, and Dandliker, et. al, 1997, for a statement of current problems now being investigated related to the electrical characteristics od DNA. The template particulate matter described herein may be used to make electrical connections to DNA and to otherwise control the structure of DNA and DNA-like molecular structures as is evident from FIGS. 1, 2, and 3 in the above description.

As previously stated in the first paragraph of the application, U.S. Disclosure Document No. 412788 was filed on the date of Feb. 10, 1997, and it was explicitly ". . . included herein in its entirety by reference . . . ". That U.S. Disclosure Document is entitled "Method and Apparatus to Create Primordial Life from Inanimate Materials". The inventor, otherwise also identified as the "author" in that U.S. Disclosure Document, has included certain excerpts from U.S. Disclosure Document No. 412788 that are substantially quoted below. Certain underlines, and other informalities in that U.S. Disclosure Document have been edited so as to properly conform with rules governing specification. In the following the inventor, or author, sets forth his own personal theories on how primordial life evolved in the early atmosphere of the earth. These personal theories have a bearing on the methods of operating the Electro-Particle Reactor as described earlier. These theories may also be used in part to distinguish the author's work from that of Miller, 1953; Miller and Urey, 1959; and from Cowen, 1995. The author's theories on the evolution of primordial life in the early atmosphere of the Earth were conveniently divided into certain subtopics to enhance readability in U.S. Disclosure Document No. 412788. Those subtopics are used herein and are listed as follows:

(a) Motivation for this Work;
(b) Several Central Suppositions;
(c) Background Information Provided by Cairns-Smith, 1985;
(d) Background Information Provided by Aldridge, 1996;
(e) A Specific Example Involving an Electrically Layered Material Acting as a Template for the Creation of DNA-like Molecules in the Atmosphere of the Earth;
(f) Advantages of Charged Particles in the Atmosphere as Templates or Catalysts for the Creation of Primordial Life;
(g) "Oil Drop Primordial Life" in Earth's Early Atmosphere—A Speculation by the Author; and
(h) Author's Forthcoming Book on this Subject.

(a) Motivation for this Work—The origin of life is certainly one of the great unresolved scientific mysteries of our times. Consider the furor in the popular and scientific press concerning the meteorite called "Alan Hills 84001" found in Antarctica and studied by NASA scientists. As stated in the press conference on Aug. 6, 1996, that particular meteorite is theorized to be from Mars and is further theorized as having indications of early life. The publicity involving this meteorite provides an ample demonstration of the worldwide interest in this topic.

The author has been working on this subject for some time in his spare time during evenings and weekends. For example, the first earlier document described above was witnessed and understood before the announcement by NASA. However, the recent coincidental publicity involving Alan Hills 84001 and the related intensified interest in this general area of science has accelerated the author's motivation to render these ideas and related inventions into writing at this particular time.

Regardless of the profound nature of the scientific inquiry, understanding the origin of life could also have great economic impact. Today's bioengineering industry is a multibillion dollar industry dedicated to designing, making, and selling various biologically active compounds. If the origin of life were understood, new and efficient methods of designing, fabricating and manufacturing such biologically active compounds would inevitably follow such a scientific breakthrough. Consequently, the author is motivated not only by the scientific matter at hand, but also by the considerable commercial potential if the origin of life were properly understood.

(b) Several Central Suppositions—To clearly set forth the author's ideas with a minimal fuss, several "suppositions" are set forth in the following.

The author has a fundamental, underlying working hypothesis that life is a robust phenomenon in the universe. A natural consequence of this hypothesis is that primordial life would have spontaneously developed on Earth as soon as the geophysical conditions on the Earth would allow any type of life whatsoever to develop. If this statement were generally true, it would have profound influence on the theory of the development of primordial life on Earth.

Therefore, the author sets forth the following major supposition of this work:

Supposition No. 1: Primordial life spontaneously developed on Earth as soon as the geophysical conditions on Earth would allow any type of life whatsoever to develop.

The term primordial life must be defined. Cairns-Smith, 1985, page 125, eloquently argues that the fundamental nature of "life" is the ability for "organisms" to "take part in the process of evolution through natural selection". In turn, that evolutionary process absolutely requires "a store of genetic information" that is a "library" of sorts which has lists of "items of information, conveniently called genes". That genetic information is expressed as a "phenotype" that is the organism's "outward and visible parts, the effect or expression of its genetic information".

In terms of describing modern organisms, any molecular form resembling DNA and any means to replicate that form of DNA shall be defined to mean "primordial life" in this work. Any molecule having the structure or general properties of DNA shall hereinafter be called a "DNA-like molecule". RNA, for example, is a DNA-like molecule for many of the purposes of this work. Consequently, the author sets forth the following:

Supposition No. 2: The creation of primordial life is equivalent to the creation of any naturally occurring means capable of assembling and replicating DNA-like molecular structures which may take part in any type of evolutionary process that allows the DNA-like molecular structures to change in time.

It is presently widely assumed that life on Earth developed in the oceans, or in hydrothermal vents within the oceans, or perhaps in hydrothermal vents on land. For additional information, see the "Background Information" below. The author certainly agrees that complex life forms including the cyanobacteria, other more complex prokaryotes, and the eukaryotes have a lineage that derives from a life form, or life forms, that lived and evolved at one time or another in the oceans.

The earliest life form having DNA and/or RNA that served as the ancestor for all modern life is called the "progenote" by some experts in the field. For more on the progenote, see for example Sogin, 1994, FIG. 4 (on page 191). It may be that the Progenote evolved in the early oceans from the primordial life defined above. However, that does not necessarily mean that the primordial life defined above originated or necessarily underwent early evolution within the oceans.

The oceans appeared at a time when the Earth's surface had cooled to the point that liquid water could condense on the surface of the Earth. Before that point in time, most of the water that eventually appeared in the oceans was in fact in the early atmosphere of the Earth in the form of steam, water droplets, clouds, etc.

There are several bench marks in the historical formation of the Earth that are widely accepted by the scientific community. Many authors hold that the Earth was formed between 4.5 to 5.0 billion years ago. Many authors also hold that very primitive life on Earth dates back to about 3.8 billion years ago. It is generally accepted that bacterial activity dates back to about 3.5 billion years ago as evidenced by stromatolites. Multicellular organisms first appeared about 500 million years ago, and the first land plants came along about 350 million years ago. For example, see Aldridge, 1996, pages 78 and 87.

It is further theorized that Earth was being bombarded by very large meteorites up to perhaps 3.8 billion years ago (Sleep, et. al., 1989). It is widely hypothesized that the cratered surface of the Moon shows the remnants of that violent history, whereas the molten surface of the Earth before that time has effectively masked that bombardment.

The author wishes to point out that it is also generally theorized, explicitly, or implicitly, that the entire surface of the Earth was a molten cauldron of rock at a time before the formation of the oceans on Earth. It appears very likely that at least a minimum of several hundred millions of years, and perhaps a billion years, intervened between the initial formation of the planet Earth from dust and interstellar debris to the time when the surface of the Earth was still comprised of molten rock.

Much of the water present in today's oceans came from interstellar dust, comets, and from chemical reactions when the molten rock within the Earth heated up thereby liberating water from naturally hydrated mineral compounds. The point is that before the oceans formed, there were vast quantities of water, dust, and chemical debris in the Earth's atmosphere for hundreds of millions of years, perhaps a billion years, before the Earth's oceans were formed. This water, dust, and chemical debris were at times subject to reasonable temperatures at various altitudes in the early Earth's atmosphere where primordial life could have evolved. Therefore, in accordance with Supposition No. 1 above, the author hypothesizes that primordial life developed as soon as possible—and that event occurred in the early atmosphere of the Earth.

As a consequence, the author sets forth the following:

Supposition No. 3: Primordial life on Earth developed in the cauldron of water, vapor, dust, and the chemicals present in the Earth's early atmosphere.

Under Supposition No. 3, there are logically three different "pathways" to the emergence of life that are listed as follows:

Pathway A: Primordial life on Earth developed in the Earth's atmosphere before the oceans were formed.

Pathway B: Primordial life on Earth developed in the Earth's atmosphere just as the oceans were forming.

Pathway C: Primordial life on Earth developed in the Earth's atmosphere after the oceans were formed.

This view is certainly contrary to the wisdom the author has found in the literature. For example, regarding the possible development of primordial life in the atmosphere, Cowen, 1995, page 17, states the following:

"Life may have begun from organic molecules that formed high in the atmosphere, but there are three major problems with this suggestion: gas molecules diffuse rapidity, so active molecules cannot be concentrated for long; any reaction products are exposed to intense solar radiation; and most complex organic molecules are dense and would fall out of the atmosphere, or be rained out. Similar objections apply to theories of life in the clouds of Jupiter, Saturn, or Titan."

The statement "life may have begun from organic molecules that formed high in the atmosphere", Cohen, 1995, was probably referring to the famous laboratory experiments conducted by Stanley L. Miller and Harold C. Urey that resulted in the production of certain amino acids and other organic molecules by passing sparks through gasses hypothesized to be present in the Earth's early atmosphere. Please refer to Miller, 1953 and to Miller and Urey, 1959. Therefore, Cohen, 1995, discounts the possibility that primordial life may have developed in the Earth's early atmosphere.

The author hypothesizes that statements such as made by Cohen above overlook the importance of electrically charged particles in the Earth's atmosphere, particularly at a time when the then entire evaporated ocean of the Earth was in the atmosphere. It is therefore important to independently consider the three particular objections raised by Cohen, 1995, above in light of the suggested importance of charged particles to the formation of primordial life.

Concerning Cohen's first statement involving hypothetical problems with diffusion and concentration, highly charged dust particles in the atmosphere can concentrate molecules for long durations of time as described in considerable detail in the forthcoming section entitled "A Specific Example Involving an Electrically Layered Material Acting as a Template for the Creation of DNA-like Molecules in the Atmosphere of the Earth" and the following section entitled "Advantages of Charged Particles in the Atmosphere as Catalysts for the Creation of Primordial Life".

Concerning Cohen's second statement involving hypothetical problems with solar radiation, reaction products produced might indeed be subject to radiation at extreme altitudes. However, if the entire ocean were in the atmosphere, the lower altitudes would be substantially shielded from harmful UV and other types of solar radiation.

Concerning Cohen's third statement involving the hypothetical problem of dense molecules falling out of the atmosphere after formation, the author suggests the following. During the initial formation of the planet significant water "outgassed" from the interior of the then molten Earth that would provide outward flowing steam that could suspend heavy dust particles and molecules in the atmosphere. And if the Earth were still very hot, the violent updrafts would continually circulate even relatively heavy dusts and molecules in the atmosphere for long periods of time.

Some aspects of this last point has been studied by Chang, 1994, FIG. 1 (page 15). He studied the vaporization of the ocean following a planetary impact. Chang, 1994, concludes that it would take thousands of years for the ocean to "rain" to the Earth following the impact of a 500 km object. Such a collision also results in "100 atmospheres of rock vapor at several thousands of degrees" for a duration of several months following impact.

Therefore, the author suggests that the three statements by Cohen above and related statements by other authors must be entirely reconsidered in light of this work.

Such considerations bring up other important questions. Were the oceans formed just one time after the Earth cooled? Or, after a first primeval ocean formed, was it vaporized once? Have the oceans been vaporized N times? Only one thing is certain. The present ocean on Earth formed after one last great cataclysmic rainfall. In this work that is called "The Last Great Condensation". This is akin to "Pathway B" above, but those pathways must be modified to include the possibility that the oceans have been vaporized, perhaps many times in the past.

Therefore, Pathways A, B, and C above must be suitably re-defined to respectively Pathways A', B', and C' as follows:

Pathway A': Primordial life on Earth developed in the Earth's atmosphere before The Last Great Condensation.

Pathway B': Primordial life on Earth developed in the Earth's atmosphere during The Last Great Condensation.

Pathway C': Primordial life on Earth developed in the Earth's atmosphere after The Last Great Condensation.

For the reasons set forth below, the author hypothesizes that Pathway B' is the most likely route by which primordial life first developed on Earth. In any event, the possible sources of charged dust fragments in the atmosphere include asteroid impacts, comet impacts, volcanos, tornados, hurricanes, etc.

The author notes that dust particles in today's atmosphere are routinely surrounded by water droplets and form clouds—an every day occupance. That such dust particles in the atmosphere are routinely surrounded by water droplets is a very important concept to the forthcoming line of reasoning. However, bare charged particles of either electric sign also frequently occur in today's atmosphere.

Electric charges and electric fields are central to the workings of life on Earth. Stryer, 1995, page 7, states: "Reversible molecular interactions are at the heart of the dance of life. Weak, noncovalent forces play key roles in the faithful replication of DNA, the folding of proteins into intricate three-dimensional forms, the specific recognition of substrates by enzymes, and the detection of signal molecules. Indeed, all biological structures and processes depend on the interplay of noncovalent interactions as well as covalent ones. The three fundamental noncovalent bonds are electrostatic bonds, hydrogen bonds, and van der Walls bonds. They differ in geometry, strength, and specificity. Furthermore, these bonds are profoundly affected in different ways by the presence of water."

The electrostatic bonds, the hydrogen bonds and the Van der Walls bonds are described in detail on pages 7–8 of Stryer, 1995, which is incorporated herein by reference.

In fact electric fields are used to separate DNA fragments in the biotechnology industry every day by using electrophoresis gels. For example, the typical Maxam and Gilbert Method and the Sanger Method are used to provide DNA sequences. These and other techniques of using electrophoresis gels appear in Lee, 1991, Chapter 7. The basic point here is that it is firmly established that electric fields strongly interact with certain DNA fragments.

Consequently, in view of the previous suppositions, the author sets forth the following:

Supposition No. 4: Electrically charged particles of mineral materials were important to the formation of primordial life in the Earth's early atmosphere.

The author further hypothesizes that particular varieties of atmospheric dust particles were critically important to the development of primordial life. A dust particle having variable electrical characteristics along one axis shall be called an "electrically layered material" abbreviated as an "ELM" in this work. A collection of such "electrically layered materials" would be called a collection of "ELMS" in this work. Examples of ELMS include layered silicates, clays, shales, etc. Further examples of ELMS include many types of minerals having repeating planar structures with differences between the adjacent planar structures—including the kaolinite and mica type minerals. ELMS in the atmosphere that may, or may not be surrounded by water droplets are acted upon by very large electric fields.

As we know from every day experience, these electric fields in the atmosphere are often strong enough to result in lightning discharges. It is widely theorized that the electric fields causing lightning in thunderheads arise because of the negative charges that build up on the updraft-suspended large hail fragments at lower altitudes caused by the friction generated by the vertical motion of lighter and smaller ice crystals that carry positive charges to higher altitudes. This process is graphically described in a recent video production (Burke, 1996). Perhaps the Earth's early atmosphere just before and during The Last Great Condensation could be characterized as some sort of persistent, world-wide thunderstorm.

Accordingly, the author sets forth the following additional supposition:

Supposition No. 5: Electrically layered dust particles, perhaps surrounded by water droplets or other fluids, which are subjected to electric fields in the Earth's early atmosphere, functioned as catalysis and/or templates for the fabrication of biopolymers in the atmosphere including DNA-like molecular structures, and certain proteins.

Before describing in detail the advantages that charged particles provide in the Earth's early atmosphere for the creation of primordial life, it is first convenient to review two references that are critically pertinent to this work.

(c) Background Information Provided by Cairns-Smith, 1985—Chapter 15 of Cairns-Smith, 1985, that is entitled "Summing-up: The seven clues", argues the following points:

In the "First clue: from biology", it states that "Genetic information is the only thing that can evolve through natural selection because it is the only thing that passes between generations over the long term."

In the "Second clue: from biochemistry", it states that "DNA is a suburban molecule far from the center of the present biochemical pathways. The same can be said of RNA. Biochemically as well as chemically these are evidently difficult molecules to make: it takes many steps to manufacture even just their nucleotide units from the simpler central molecules of biochemistry. All this suggests a comparatively late arrival for these now undisputed rulers."

In the "Third clue: from the building trade" relates to the "likelihood of a missing agent, and earlier 'scaffolding'—an earlier design of organism at the start of evolution."

In the "Fourth clue: from the nature of ropes", it points out that "None of the fibres in a rope has to stretch from one end to the other, so long as they are sufficiently intertwined to hold together sideways. The long lines of succession that alone connect us to distinct ancestors are like multi-fibred ropes in that what are passed on between generations are collections of genes ('intertwined' because they correspond to variable organisms and it is thus in their mutual interest to stay together)."

In the "Fifth clue: from the history of technology", "Primitive machinery is usually different in its design approach (and hence in materials of construction) from later advanced counterparts. The primitive machine has to be easy to make from immediately available materials; and it must work, more or less, with minimum of fuss." This clue further states: "This fifth clue led us to suspect that the first, unevolved (necessarily 'low-tech') organisms would have been very different from the (manifestly 'high-tech') organisms of today. Most probably their materials of construction would have been very different too."

In the "Sixth clue: from chemistry" it states that "Crystals put themselves together, and in a way that might be suitable for 'low-tech' genetic materials. Even the most primitive kind of gene-printing process would have to be fairly precise and involve the coming together of a fair number of atoms. Big organic molecules show little sign of having the appropriate self-control." This clue further states: "The sixth clue gave a sense of direction to our search for primitive biochemical materials."

In the "Seventh clue: from geology", that clue is entirely quoted as follows: "The Earth makes clay all the time, as you can see from the huge amounts of it that are carried in rivers. The minerals of clay are tiny crystals that grow from water solutions derived from weathering of hard rocks. Not only for primitive genes, but also for other primitive control structures such as 'low-tech' catalysts and membranes, these kinds of inorganic crystals seem to be much more appropriate than big organic molecules." That clue continues with the next paragraph: "The seventh clue depends for its significance on all others. It is certainly no new idea that this most earthly of materials, clay should have been the stuff of first life—it is in the Bible. What is new is our understanding of just how interesting, varied and complicated this sort of stuff is when looked at under a super-powered magnifying glass. The seventh clue appeared in chapter 11."

The ideas, concepts, and definitions are explicitly included herein by reference from Cairns-Smith, 1985, with particular note to the following: "Appendix 1" that describes "Units for DNA and RNA" and "Units for Proteins"; "Appendix 2" that describes "The kaolinite layer", "The (ideal) muscovite mica layer" and "Units for Clay crystals"; and the "Glossary" for "Part I" and "Part II". The author shall utilize the definitions herein as provided in the Glossary of Cairns-Smith, 1985.

A major point of Cairns-Smith, 1985, is that clay is somehow involved in the evolution of life as we know it on this planet. However, Cairns-Smith, 1985, states in Chapter 13, on the bottom of page 10 the following: "For example, clay crystals growing in the pores within a piece of sandstone might very well turn out to be the primary organisms." It further states on page 101: "The shapes and sizes of clay crystals can greatly affect the porosity of a sandstone that contains them." Much detail is presented about clays within the Earth by Cairns-Smith, 1985, and in particular on page 102 it suggests illites as a possible candidate, which tend "to clog up oil-bearing sandstones".

Importantly, Cairns-Smith, 1985, clearly describes and suggests that the hypothetically life-forming clays are subterranean. To the knowledge of the author, there is no indication or suggestion at any point by Cairns-Smith, 1985, that the clays are airborne in any way, nor is there any indication or suggestion that electric fields acting on such airborne clays are of importance to the formation of primordial life. The author knows of no suggestion whatsoever in Cairns-Smith, 1985, that primordial life could have emerged in the atmosphere of early Earth.

(d) Background Information Provided by Aldridge, 1996—Chapter 4 in Aldridge, 1996, is entitled "Where did DNA come from?". That chapter reviews many modern theories concerning the origin of life which are current as of 1996, when the book was published.

Chapter 4 of Aldridge, 1996, begins by describing several unrelated theories. Page 77 states: "Creationists—who believe that God put each species on Earth fully formed—are conveniently sidestepping one of the toughest problems in science, that of how life began. Charles Darwin developed a convincing theory of how the earliest life forms evolved into more complex organisms. But he could not say how the first organism—often called the progenote—arose."

Page 79 of Aldridge, 1996, describes the work done by Harold Urey and Stanley Miller in the 1950's. A passage from that page is quoted as follows: 'Urey and Miller's experiments were based on earlier ideas about the origin of life put forward by J. B. S. Haldane working in Oxford, and the Russian chemist Alexander Oparin. They argued that life had emerged from a "hot dilute soup" (in Haldane's words). To do this they circulated methane, ammonia and water though a system of flasks and tubes. From time to time they bombarded this mixture with electrical sparks, which were meant to simulate the intense solar radiation that was a key feature of the young Earth.' The next paragraph begins with: "After a few days of all this the liquid that Urey and Miller were pumping round the system contained glycine—one of the essential amino acids. So the building blocks of life could well have merged from the raw materials available at the time." However, the author is unaware of any use of electrically layered materials by Urey and Miller to act as catalysts and/or templates to create biopolymers including such compounds as DNA, RNA, and certain proteins.

Aldridge, 1996, further states on page 80: "But shock waves from meteoric and cometary impacts, and intense ultraviolet light from the Sun (there was no ozone layer to absorb it because there was no free oxygen), were hardly conductive to the orderly assembly of these building blocks into nucleic acids and proteins. Even in a quiet corner of a chemistry laboratory you need sophisticated reagents and controlled chemistry to make these biopolymers from the component parts. Just mix them in a test tube and you will get nothing, or things will go too far, resulting in a nasty black tar".

Chapter 4 of Aldridge, 1996, page 80, further states: "So a number of intriguing hypotheses have been suggested to explain the evolution of biopolymers. One that has been promoted in recent years by John Corliss of the National Aeronautics and Space Administration (NASA) and several other scientists is that the primordial soup was formed in hydrothermal vents, rather than on the Earth's surface." The next paragraph goes on to state: "It is hard to say how far life could have progressed under these conditions, but the proposal has been lent powerful support by the discovery of bacterial communities in hydrothermal vents. These microbes belong to a group called Archaebacteria, which have been identified by American scientist Carl Woese has having ancient origins and are discussed in detail later in this chapter. Indeed many Archaebacteria have been found in 'primitive' surroundings that resemble our ideas about the early Earth (low in oxygen, for example)."

Chapter 4 of Aldridge, 1996, prominently discusses Cairns-Smith, 1985, and its implications. Pages 80–81 of Aldridge, 1996, describes the work by Cairns-Smith as follows: "He has developed the idea of an early stage in the hallmark of life as we know it as assembling on these catalytic clays. Clay contains silicon, which is in the same chemical group as carbon—on which life is based. Minerals are crystals that replicate their regular inner arrangement of atoms as they grow. Clay minerals can 'mutate' says Cairns-Smith, by accumulating imperfections in their crystals, which are then replicated. Even simple crystals such as those of zinc or iron will acquire these imperfections. There might be a hole in the regular arrangement of metal atoms, or a place where an extra atom has crowded in. In the case of complex minerals such as Cairns-Smith's silicates, these 'mutations' could eventually produce some form of catalytic activity. He visualizes the organic building blocks that are the hallmark of life as we known it as assembling on these catalytic clays. Eventually carbon-based life took over from silicon-based life, says Cairns-Smith, who has coined the term 'genetic takeover' for the transition from clay to DNA." However, Aldridge, 1996, describes and suggests that the hypothetically life-forming clays are subterranean. To the knowledge of the author, there is no indication or suggestion at any point in Aldridge, 1996, that the clays are airborne or otherwise atmospherically based; nor is there any indication or suggestion in Cairns-Smith, 1985, or in Aldridge, 1996, that electric fields acting on such airborne clays are of any importance or significance to the origin of life on Earth.

Chapter 4, page 81, of Aldridge, 1996, goes on to state: "More recently, Cairns-Smith has joined with other colleagues in Glasgow, such as Michael Russell, in speculating that life could have emerged from bubbles of iron sulphide (a common mineral sometimes known as 'fools' gold') in alkaline springs on the ocean floor."

Chapter 4, page 81, of Aldridge, 1996, further states: "Indeed, Christian de Duve of Rockefeller University has suggested that simple compounds of sulphur, carbon and oxygen (called thioesters), which formed in hydrothermal vents, might have triggered some crude early form of biochemistry."

Chapter 4, page 81, of Aldridge, 1996, states: "Other scientists have avoided facing up to the problem of how molecules of life were built on Earth by saying they came from outer space! Recent space explorations have focussed attention on the ideas of Fred Hoyle and Chandra Wickramasinghe, who have developed the concept of panspermia—life being 'seeded' by microbes falling from cometary dust. Few scientists believe this, but the discovery of organic compounds such as amino acids in interstellar dust, meteorites, and Halley's comment suggests that the Earth may have been sprinkled with at least with life's building blocks—if not fully formed organism—in the dusts of meteoric impact."

The author is indebted to Susan Aldridge for properly "setting the stage" for the following. The First, Second, and Third Stages are identified by my notations of "{First Stage}", "{Second Stage}", and "{Third Stage}" which have been respectively added to the following quote. Page 79 of Aldridge, 1996, states: "The origin of life is usually seen in three distinct stages. First {First Stage}, there has to be generation of basic organic building blocks such as nucleotides and amino acids. Next {Second Stage} comes assembly of these building blocks into functional polymers DNA, RNA and proteins (this is generally reckoned to be the hardest thing to explain). Self-replication (nucleic acids) and catalysis (enzymes) are the chemical processes which got life going {Third Stage}."

The First Stage above can be visualized as having been solved in-principle by the work of Harold Urey and Stanley Miller.

The Third Stage above can be visualized as being solved in-principle in light of the following quote from Aldridge, 1996, page 82, as follows: "Once there were nucleic acids and proteins around, however primitive, they would have tended to reorganize themselves into cells. There is an explosion of interest today in the way big molecules sometimes self-organize into droplets and sheets. This behavior was noticed many years ago by Alexander Oparin, who demonstrated the formation of cell-like entities from the protein gelatin and gum arabic, a carbohydrate. These droplets, known as coacervates, let substances pass in and out of their membranes. If you put enzymes inside them, they will catalyze simple reactions. Eventually these first cells may have evolved into the first single-cell organism with a DNA genome. This is called the progenote and it is the ancestor of us all. It has left no trace, but with its emergence the stage was set for the story of the evolution of DNA to commence."

Heretofore, the present state of knowledge has NOT adequately addressed the "Second Stage" identified above.

To repeat, and to emphasize, a major purpose of this work is to address the challenge set forth by Susan Aldridge: "Next {Second Stage} comes assembly of these building blocks into functional polymers—DNA, RNA and proteins (this is generally reckoned to be the hardest thing to explain) ."

The ideas, concepts, and definitions are explicitly included herein by reference from Aldridge, 1996.

It should be noted that both Cairns-Smith, 1985, and Aldridge, 1996, describe "primordial soups". For the record, no references known to the author suggest that airborne clays and shales acted upon by electric fields are of importance in the creation of life on this planet. The author will substantially elaborate on this point in the following, but it is first necessary to introduce the concept of airborne electrically layered materials.

The author shall rely upon the standard terms and up-to-date knowledge in the field of biology and bioengineering in the remainder of this work. The ideas, concepts, and definitions from every one of the cited References are included herein by reference in their entirety without further quotes.

(e) A Specific Example Involving an Electrically Layered Material Acting as a Template for the Creation of DNA-like Molecules in the Atmosphere of the Earth—This is a specific representative example so that the author's ideas can be clearly set forth. It is improbable that the following will turn out to be the best path or the optimum path for the creation of primordial life on Earth. Nevertheless, the author must begin somewhere with a concrete example of a mechanism that could work.

Suppose that a first primeval ocean had formed. Then it was vaporized by an asteroid a first time. Then the ocean re-formed. Then it was vaporized by a second asteroid a second time. Then, The Last Great Condensation began.

Certain forms of clays or shales would certainly be present within the atmosphere during The Last Great Condensation. After all, they were formed in the several earlier primeval oceans. Dewan, 1983, page 230 points out that a shale "is a mixture of clay minerals and silt laid down in a very low-energy environment, principally by settlement from still water." He goes on to say: "The solids of a typical shale may consist of about 50% clay, 25% silica, 10% feldspar, 10% carbonates, 3% iron oxide, 1% organic material and 1% other material." Of course, any early shale in the Earth's atmosphere might not have the same type of "organic material" present that is referenced by Dewan. According to Dewan, "shale may also contain 2–40% water by volume".

Dewan, 1983, page 230, further states: "Clay particles have a layered platelet structure. The crystalline platelets are very thin, 5–10 A, but may extend to about 10,000 A in length or width. They are stacked one above the other with spacing between them of 20–100 A. The clay particles are therefore extremely small—about 2 u in maximum dimension." (Here A stands for the angstrom unit and u stands for the micron unit.) The point is that shale is comprised of very thin laminated layers.

As noted above, the atmospheric fabrication of nucleotides has not been demonstrated so far in Miller—Urey type experiments. See Cowen, 1995, page 12. However, the author suggests that another experiment be performed to test this hypothesis with the EPR. Here, however, the source of organics would be chosen to be the separate phosphate, sugars, and a base that comprises one of the 4 nucleotides. Then, a similar experiment may be run to that just described above. Though actual nucleotide fabrication has yet to be successful, the author wishes to quote the following passage from pages 11–12 of Cowen, 1995:

"Nucleic acids (RNA and DNA) have structures made up of nucleic acid bases, sugars, and phosphates. Nucleic-acid bases form from cyanide in experiments that simulate lightning strikes on the early Earth. The base adenine has a structure formed easily by rearranging five HCN molecules . . . , but the formation of other bases from cyanide mixtures was a pleasant surprise. Cyanide reactions are promoted by the presence of formaldehyde, which was also produced in abundance in the early atmosphere. The reactants work best in half-frozen mixtures . . . Sugars have been formed in laboratory conditions simulating the flow of water from hot springs over beds of clay. Naturally occurring phosphate minerals were available for such reactions from volcanic activity. This all the ingredients for nucleic acids were present on the early Earth, and the universal cell ATP could have formed easily in the early Earth."

The point is that step, by step, the EPR can be used to answer whether or not atmospherically based charged particles may be used as catalysis or templates for various types of biologically active molecules. In particular, the apparatus shown in FIG. 10 comprised of four EPR's in sequence can be used to simulate the generation of primordial life on Earth from scratch. Clearly, the EPR may be used to experimentally test the author's hypotheses that primordial life developed in the early atmosphere of the Earth.

After positive results are obtained with the above experiments, and elaborations thereof, the EPR will then become of considerable commercial importance. By carefully choosing the parameters of the EPR, the type of particulate matter and the input chemicals, many different commercially valuable compounds may be suitably synthesized with the EPR for the biotechnology industry.

(f) Advantages of Charged Particles in the Atmosphere as Templates or Catalysts for the Creation of Primordial Life— One of the most significant advantages for the creation of DNA-like molecular structures in the atmosphere involves everyday experience in the biotechnology industry. Aldridge, 1996, on page 7 states: ". . . —time has shown that DNA is a fragile molecule, and this is why chilling is so important in the extraction of DNA from the onion, described at the beginning of this chapter (and why a bucket of ice is a vital accessory for all self-respecting molecular biologists)". Stryer, 1995, on pages 84 through 87 shows that DNA melts at temperatures ranging from 77 degrees C. to about 100 degrees C. Atmospheric processes allow the possibility of rapid temperature cycling, which is generally not possible under alternative suggestions for the creation of primordial life on Earth. If one imagines a small drop of water in the atmosphere, it may stay a liquid, freeze into small ice particles, or become a part of a large hailstone. This is true today, and at certain altitudes, would have been true during the period of The Last Great Condensation.

Aldridge, 1996, goes on to state of page 80: "Even in a quiet corner of a chemistry laboratory you need sophisticated reagents and controlled chemistry to make these biopolymers from their component parts. Just mix them in a test tube and you will get nothing, or things will go too far, resulting in a nasty black tar." If one imagines a small drop of water in the atmosphere, it can hypothetically have almost any possible concentration of constituents in the small droplet. For example, if a bit of salt were blown into the atmosphere by a volcano, and when hydrated, it could become supersaturated. Similarly, any given small drop could conceivably have any reasonable concentration of any soluble component—all subject to the laws of probability.

If one further imagines small droplets of water as being equivalent to "imaginary test tubes in the sky", then it is clear that, in principle, any one such "imaginary test tube" can be at just about any reasonable temperature from 0 degrees C. to 100 degrees C., can be cycled rapidly in temperature as the drop goes up or down in altitude, and it can have just about any type of mineral dissolved in it. The author is unaware of other modes in the development of primordial life on Earth which has this property.

Proponents of the development of primordial life in the early oceans seem to forget that water by itself is damaging to DNA by itself. For example Cowen, 1995, page 12 states: "Linking sugars, phosphates, and nucleic-acid bases to form fragments of nucleic acid called nucleotides is also a dehydration process and the phosphates themselves can act as catalysts here." Droplets of water surrounding charged particle templates can evaporate in the atmosphere resulting in such a dehydration process. It is not clear how DNA-type molecular structures could have evolved first in the early oceans if water destroys DNA.

Atmospheric process can concentrate various chemicals by evaporation, concentration by freezing, concentration in small droplets, concentration on mineral grains, etc.

A considerable advantage of charged particles acting as templates in the atmosphere comes from electrostatic arguments. Stryer, 1995, states on page 7:

"A charged group on a substrate can attract an oppositely charged group on an enzyme. The force (F) of such an electrostatic attraction is given by Coulomb's law:"

$$F=(q_1 q_2)/(r^2 D)$$

"in which $q_1$ and $q_2$ are the charges of the two groups, r is the distance between them, and D is the dielectric constant of the medium. The attraction is strongest in a vacuum (where D is 1) as is weakest in a medium such as water (where D is 80). This kind of attraction is also called an ionic bond, salt linkage, salt bridge, or ion pair."

The point is that electrically charged particles in the atmosphere produce forces that are 80 times greater on other charged fragments than would be the case in water. Therefore, there is a much greater tendency for electrically charged particles in the atmosphere to collect or concentrate other charged fragments than would be the case in an ocean environment. This logic can be verified in part using everyday experience: a dust mop works great in air, but works poorly in water.

We intrinsically know that phosphates and dust particles "dirt" have an everyday relationship. Aldridge, 1996, states on pages 9–10: "The reason why phosphates are present in detergents is that they stop dirt settling back into fabric once it has been removed." Therefore, it is certainly reasonable to assume that the phosphate in nucleotides would have a tendency to react strongly with any clay particles in the EPR and in the Earth's early atmosphere as described earlier.

It is known that ultraviolet light is damaging to DNA. However, if during The Last Great Condensation the entire oceans were in the atmosphere in the form of steam and water droplets, then ultraviolet light would not penetrate to great depths within such an atmosphere.

There is a further step to take at this point. Is it possible that primordial life actually developed entirely in the Earth's early atmosphere?

(g) "Oil Drop Primordial Life" in Earth's Early Atmosphere—A Speculation by the Author—The author wishes to set the stage for this speculation. Assume that the Earth is in a period just before The Last Great Condensation. At that time, significant water was "outgassing" from the interior of the then molten Earth that would provide outward flowing steam that could suspend heavy dust particles and molecules in the atmosphere. Because the Earth at that time was still very hot, the violent updrafts would continually circulate even relatively heavy dusts and molecules in the atmosphere for long periods of time. Could atmospheric conditions exist for the suspension of heavy dust particles and molecules in the atmosphere for long periods of time? Perhaps it is best to answer this with a question. If the red "eye" of Jupiter has been at the same place for hundreds of years, in principle, why couldn't such updrafts exits for long periods of time?

Speculating further, what happens if lipids are introduced into an EPR in the above experiment involving the creation of DNA-like molecular structures? Is it possible that the EPR would produce lipid covered DNA-like molecular structures? According to the analysis of the "{Third Stage}" of the work of Aldridge, 1996 (particularly in relation to page 82), such an outcome would perhaps inevitably lead to the development of primordial life. What could this form of primordial life be?

Perhaps such primordial life would resemble an "oil drop" type substance suspended in the upwelling steam and gases. This brings to mind the famous "oil drop" experiment first performed by Millikan to determine the charge of the electron. See Harnwell and Livingood, 1933, pages 98–108. That analysis shows that the force on a spherical object is proportional to its relative velocity with respect to the air flowing by it. Such buoyant forces could indefinitely suspend an "oil drop" type substance before The Last Great Condensation.

Speculating further, could "oil drop primordial life" have evolved in the early atmosphere of the Earth? Take the case of an oil drop having a dust particle, some DNA, some water, and a given radius. If too heavy under the upwelling, it will drop to lower altitudes. If too light, it will raise to higher altitudes.

If the oil drop is too heavy, it will drop in altitude. Consequently, it will then heat up. The DNA present will then melt, denature, or "unwind" into its separate strands. Maybe the oil drop splits into two fragments, each having separate strands of DNA. Then the lighter fragments would go up into the atmosphere. Maybe each separate unwound DNA strand in each separate drop would then cool, and self-assemble into helical form from other fragmentary nucleotides in the atmosphere. Then, the DNA has essentially reproduced itself. Then its increased weight after reproduction is such that the new drop it will go down in altitude so that the DNA will melt again. This could go on and on. This process would be subject to long term evolutionary changes in the molecular structure of the DNA in the oil drops. This is an example of a type of primordial life that develops entirely within the Earth's early atmosphere. This is equivalent to satisfying Supposition No. 2 that is quoted below again in its entirety:

Supposition No. 2: The creation of primordial life is equivalent to the creation of any naturally occurring means capable of assembling and replicating DNA-like molecular structures which may take part in any type of evolutionary process that allows the DNA-like molecular structures to change in time.

For now, I will call this "oil drop primordial life". It is also known that after DNA melts at its melting temperature, that when cooled, it will again anneal back into its helical shape. See page 87 of Stryer, 1995. Other types of primordial life that depend on this phenomenon can be similarly theorized.

Speculating yet further, suppose the oil drop primordial life is to generate energy somehow. What would it use for fuel? The most likely fuel available in the Earth's early atmosphere is carbon dioxide, water and light.

The equation for photosynthesis is deceptively simple (Stryer, 1995, page 653):

$$H_2O + CO_2 \text{--light--} (CH_2O) + O_2$$

Stryer states: "In this equation, ($CH_2O$) represents carbohydrate, primarily sucrose and starch." Call this "Equation 1".

Photosyntheses seems to require those chemical constituents that appear to be in most abundance in the Earth's early atmosphere. Is this coincidence? Perhaps not. Further speculating, suppose that the ancestor of the earliest cynobacteria were actually oil drop primordial life that somehow executed photosynthesis in some form as stated in Equation 1. What would then happen?

Suppose the oil drop was too heavy at a given altitude to be suspended in the upwelling atmosphere prior to The Last Great Condensation. As the oil drop went down in altitude, the light intensity from the Sun would decrease leading to a decrease in the production of carbohydrates from Equation 1. The oil drop would tend to evaporate and lose mass. As the mass was reduced, it would then be carried to higher altitudes. There, the light intensity would increase and the production of carbohydrates would be increased. Then the oil drop would get heavier. And so it would go down in altitude. And so on, and so on—oscillating upward and downward indefinitely.

This upward and downward oscillating oil drop primordial life would then be subject to all the evolutionary pressures nature brings to bear—and this could have been the progenote for all life on Earth.

During The Last Great Condensation, the upward and downward oscillating oil drop primordial life would eventually fall from the atmosphere into the primordial oceans of the Earth. With this view, functioning primordial life falls from the atmosphere into the oceans for further evolution.

The hypotheses of upward and downward oscillating particles in the atmosphere may appear at first sight to be a radical proposition. However, it has been noted that many hail stones look like an onion inside—with many overlapping layers located radially away from the center. This type of structure indicates that hail stones often undergo such upward and downward oscillations which also involves many temperature cyclings. Therefore, everyday experience shows that upward and downward oscillations of particulate matter commonly occur in today's atmosphere. In view of these comments, perhaps oil drop primordial life in the early atmosphere of the Earth seems more plausible.

Then why do we not apparently see the spontaneous generation of such oil drop primordial life in today's atmosphere? In this case, it is easy to answer. The conditions are entirely different today than at the time just before The Last Great Condensation.

This ends the author's speculation about oil drop primordial life for the time being. Regardless of the validity of the speculations under this section, the experiments involving the Electro-Particle Reactor should be carried out as soon as possible.

(h) Author's Forthcoming Book on this Subject—The author intends to write a book on the above subject entitled "Born of Lightning and Dust".

It is now necessary for the inventor to clearly define the references that have been heretofore been abbreviated in the specification and other references which are important references to this invention, entire copies of which are included herein by reference:

Aldridge, Susan, 1996, "The Thread of Life, The story of genes and genetic engineering", Cambridge University Press, Cambridge, Great Britain Audesirk, Teresa and Gerald, 1996, "Biology, Life on Earth", 4th Edition, Prentice Hall, Upper Saddle River, N.J.

Burke, Richard, 1996, "Electric Skies", a video production written and directed by Richard Burke, made by Pioneer Productions, and shown on The Learning Channel during 1996

Cairns-Smith, A. G., 1982, "Genetic Takeover", Cambridge University Press, Cambridge, Great Britain Cairns-Smith, A. G, 1985, "Seven Clues to the Origin of Life", Cambridge University Press, Cambridge, Great Britain Campbell, K. H. S.; McWhir, J.; Ritchie, W. A.; and Wilmut, I.; 1996, in paper entitled "Sheep cloned by nuclear transfer from a cultured cell line", Nature, Vol. 380, pp. 64–66

Chang, Sherwood, 1994, paper entitled "The planetary setting of prebiotic evolution", on pages 10–23 in the book entitled "Early Life on Earth", Nobel Symposium No. 84, Stefan Bengston, editor, Columbia University Press, New York, N.Y.

Cowen, Richard, 1995, "History of Life", Second Edition, Blackwell Science, Inc., Cambridge, Mass.

Dandliker, Peter J.; Holmlin, R. Erik; and Barton, Jacqueline K.; 1997, in paper entitled "Oxidative Thymine Dimer Repair in the DNA Helix", Science, Vol. 275, pp. 1465–1468 (March 7)

Deamer, David. W. and Fleischaker, Gail R., 1994, "Origins of Life, The Central Concepts", Jones and Bartlett Publishers, Boston Dewan, John T., 1983, "Essentials of Modern Open-Hole Log Interpretation", PennWell Books, PennWell Publishing Company, Tulsa, Okla.

De Duve Christian, 1995, "Vital Dust", Basic Books, A Division of Harper Collins Publishers, Inc., New York, N.Y.

Editor, 1996, "A Dictionary of Biology", Third Edition, Oxford University Press, New York, N.Y.

Emiliani, Cesare, 1995, "Planet Earth, Cosmology, Geology, and the Evolution of Life and Environment", Press Syndicate of the University of Cambridge, Cambridge, Great Britain Ferris, James P.; Huang, Chun-Hsien; and Hagan Jr., William J., 1988; paper entitled "Montmorillonite: A Multifunctional Mineral Catalyst for the Prebiological Formation of Phosphate Esters", in Origins of Life & Evolution of the Biosphere, Volume 18, pp. 121–133

Garassino, Alessandro, 1995, "Beginnings, Life Origins and Evolution", Raintree Steck-Vaughn Publishers, Austin, Tex.

Gedulin, Benjamin and Arrhenius, Gustaf, 1994, paper entitled "Sources and geochemical evolution of RNA precursor molecules: The role of phosphate", pages 91–106 in book entitled "Early Life on Earth", Nobel Symposium No. 84, Stefan Bengston, editor, Columbia University Press, New York, N.Y.

Halliday, David and Resnick, Robert, 1978, "Physics, Parts I and II Combined", Third Edition, John Wiley & Sons, New York, N.Y.

Harnwell, G. P., and Livingood, J. J., 1933, "Experimental Atomic Physics", McGraw-Hill Book Company, New York, N.Y.

Kittel, Charles, 1967, "Introduction to Solid State Physics", John Wiley & Sons, Inc., New York, N.Y.

Lee, Thomas F., 1991, "The Human Genome Project, Cracking the Genetic Code of Life", Plenum Press, New York, N.Y.

Miller, Stanley L., 1953, paper entitled "A production of amino acids under possible primitive Earth conditions", Science, Vol. 117, pp. 528–529

Miller, Stanley L. and Urey, Harold C., 1959, paper entitled "Organic Compound Synthesis on the Primitive Earth", Science, Vol. 130, pp. 245–251

Nicholl, Desmond S. T., 1995, "An Introduction to Genetic Engineering", part of the Studies in Biology Series, Cambridge University Press, Cambridge, Great Britain Sleep, Norman H.; Zahnle, Kevin J.; Kasting, James. F.; and Morowitz, Harold J.; 1989, paper entitled "Annihilation of ecosystems by large asteroid impacts on the early Earth", Nature, Vol 342, pp. 139–142

Sogin, Mitchell L., 1994, paper entitled "The origin of eukaryotes and evolution into major kingdoms", on pages 181–192 in the book entitled "Early Life on Earth", Nobel Symposium No. 84, Columbia University Press, New York, N.Y.

Stewart, Colin, 1997, article entitled "Nuclear transplantations, An udder way of making lambs", Nature, Vol. 385, pp. 769–771 (February 27)

Stryer, Lubert, 1995, "Biochemistry", 4th Edition, W. H. Freeman and Company, New York, N.Y.

Taubes, Gary, 1997, article entitled "Double Helix Does Chemistry At a Distance—But How?", Science, Vol. 275, pp. 1420–1421 (March 7)

Watson, James D.; Hopkins, Nancy H.; Roberts, Jeffrey W.; Steitz, Joan Argetsinger; and Weiner, Alan M.; 1987, "Molecular Biology of the Gene", Fourth Edition, The Benjamin/Cummings Publishing Company, Inc., Menlo Park, Calif.

Westheimer, F. H., 1987, paper entitled "Why Nature Chose Phosphates", Science, Volume 235, pp. 1173–1178

Wilmut, I.; Schnieke, A. E.; McWhir, J.; Kind, A. J.; Campbell, K. H. S.; 1997, paper entitled "Viable offspring derived from fetal and adult mammalian cells", Nature, Vol. 385, pp. 810–813 (February 27)

In addition, those particular references cited above in this application under the topic of "References Cited" are also included herein in their entirety by reference.

This is the end of the explicit listing of the references that have been heretofore been abbreviated in the specification and other references which are important references to this invention.

While the above specification provides many particular examples, these should not be interpreted as limitations on the scope of the invention, but rather as examples of preferred embodiments of the invention. As described above, there are many possible variations. Therefore, the scope of the invention should not be determined by the embodiments illustrated and the many variations thereto, but by the following claims and any legal equivalents thereto.

What is claimed is:

1. The method to synthesize DNA and DNA-like molecular structures comprising at least the following steps:
   (a) mix predetermined nucleotides and template particulate matter together in a gaseous medium to form a gaseous mixture;
   (b) apply an electric field to said gaseous mixture to form the reaction products that include DNA and DNA-like molecular structures.

2. The method to synthesize proteins comprising at least the following steps:
   (a) mix predetermined amino acids and template particulate matter together in a gaseous medium to form a gaseous mixture;
   (b) apply an electric field to said gaseous mixture to form the reaction products within said gaseous mixture that include proteins.

3. The method to synthesize DNA and DNA-like molecular structures comprising at least the following steps:
   (a) mix predetermined nucleotides as the initial chemical reactants and template particulate matter as the catalysts together in a gaseous medium to form a gaseous mixture;
   (b) apply an electric field to said gaseous mixture to form the reaction products that include DNA and DNA-like molecular structures; whereby the intensity of said field is less than a threshold value to cause electrical breakdown in said gaseous mixture.

4. The method to synthesize proteins comprising at least the following steps:
   (a) mix predetermined amino acids as the initial chemical reactants and template particulate matter as the catalysts together in a gaseous medium to form a gaseous mixture;
   (b) apply an electric field to said gaseous mixture to form the reaction products that include proteins; whereby the intensity of said field is less than a threshold value to cause electrical breakdown in said gaseous mixture.

* * * * *